(12) United States Patent
Hodges et al.

(10) Patent No.: US 10,311,204 B2
(45) Date of Patent: Jun. 4, 2019

(54) DYNAMIC MEDICAL ECOSYSTEMS AND INTELLIGENCE MODELING

(71) Applicants: Camille Hodges, Youngsville, LA (US); Daniel Hodges, Youngsville, LA (US)

(72) Inventors: Camille Hodges, Youngsville, LA (US); Daniel Hodges, Youngsville, LA (US)

( * ) Notice: Subject to any disclaimer, the term of this patent is extended or adjusted under 35 U.S.C. 154(b) by 294 days.

(21) Appl. No.: 14/611,790

(22) Filed: Feb. 2, 2015

(65) Prior Publication Data
US 2015/0286795 A1 Oct. 8, 2015

Related U.S. Application Data

(63) Continuation-in-part of application No. 14/205,844, filed on Mar. 12, 2014, and a continuation-in-part of application No. 14/212,250, filed on Mar. 14, 2014.

(60) Provisional application No. 61/934,090, filed on Jan. 31, 2014.

(51) Int. Cl.
*G06N 7/00* (2006.01)
*G06F 19/00* (2018.01)
*G16H 50/50* (2018.01)

(52) U.S. Cl.
CPC ............ *G06F 19/00* (2013.01); *G16H 50/50* (2018.01); *G06N 7/00* (2013.01)

(58) Field of Classification Search
None
See application file for complete search history.

(56) References Cited

U.S. PATENT DOCUMENTS

2014/0378778 A1* 12/2014 Hodges ................ A61B 5/7275
600/301

* cited by examiner

*Primary Examiner* — Wilbert L Starks
(74) *Attorney, Agent, or Firm* — IPR Law Group PC

(57) ABSTRACT

Systems and methods of embodiments comprise receiving in real-time data of parameters representing an entity. Micro plots are generated, and each micro plot comprises a plot of the data for a corresponding time period of a multitude of time periods. Each time period is cyclical. A model plot is generated to include the micro plots plotted chronologically according to the time periods. The model plot comprises a continuous helix. A prediction of a state of the entity is generated using characteristics of the model plot.

18 Claims, 20 Drawing Sheets

From the Active Practice Physician Perspective

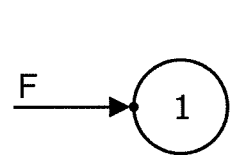
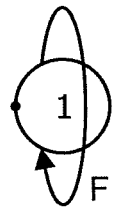
*FIG. 29(a)*   *FIG. 29(b)*
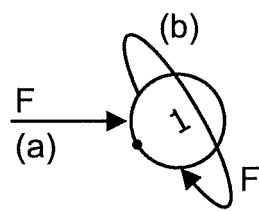
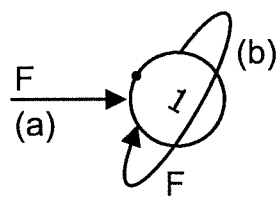
*FIG. 30*
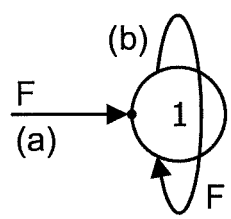
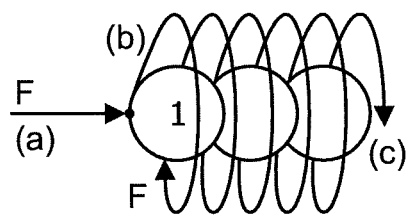
*FIG. 31*
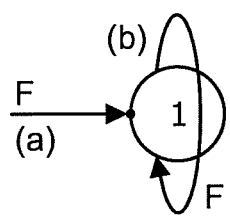
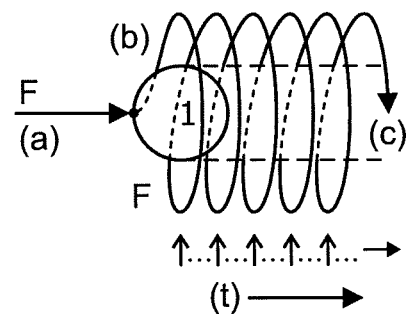
*FIG. 32*

DYNAMIC MEDICAL ECOSYSTEMS AND INTELLIGENCE MODELING

RELATED APPLICATIONS

This application claims the benefit of U.S. Patent Application No. 61/934,090, filed Jan. 31, 2014.

This application is a continuation in part of U.S. patent application Ser. No. 14/205,844, filed Mar. 12, 2014.

This application is a continuation in part of U.S. patent application Ser. No. 14/212,250, filed Mar. 14, 2014.

TECHNICAL FIELD

The embodiments described herein relate generally to systems and methods for modeling and, more particularly, to dynamic medical ecosystems modeling.

BACKGROUND

The basis for organized medicine was established in approximately 400 B.C. Since then the art and practice has essentially been one of single point probabilistic approximation and formulation. For over two-millennia brief encounters with the treating physician or their staff has represented the pillar of established medical practice and healthcare delivery. Medicine as a discipline in the 21st century clearly has had the advantage of exponential growth in healthcare technology particularly over the past thirty years, but at its very core, the physician's single point probabilistic approximation and formulation remain (differential diagnosis) all but unchanged in its 2500-year existence. There is a need for micronization of the future of medicine under a new paradigm that promises to revolutionize the practice and delivery of healthcare.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 29A shows entropic linear-forces acting upon a celestial body/mass; create fictitious pre-conceptual randomness (primary).

FIG. 29B shows entropic angular-forces acting upon a celestial body/mass; create fictitious pre-conceptual non-randomness (secondary).

FIG. 30 is a depiction of the pre-evolutional graphic of the (1) earth moving within the forming universe's accretion disk as a chaotic celestial** body transitioning to [(a)+(b)], where (a) represents a cosmic linear entropic force and (b) represents a cosmic angular entropic force, as described herein.

FIG. 31 demonstrates the transition in the late** accretion period to (c) (tertiary).

FIG. 32 depicts the sustained "after-wake" effect of cosmic entropic force acting upon [(a)+(b)] and producing the energy-driven transition to (c).

DETAILED DESCRIPTION

Figure 1:
FIG. 1 is a block diagram of an example of static moments in patient treatment practice.

The conventional practice of medicine has been one of static formulation. Static moments or points in time (much like a "snapshot" or photo) have been the basis for practicing modern medicine. For example, a physician may check a patient's blood pressure on two different occasions (office visits) over a two-week period. FIG. 1 is a block diagram of an example of static moments in patient treatment practice. The snapshot of information obtained during the two visits is then used to determine and initiate a medication regime with an antihypertensive agent. For example, a symptomatic 44-year-old overweight male patient complaining of a two-week history of fatigue and dizziness newly presents to a family physician's office at 4 pm on a Friday afternoon. His blood pressure as checked by the office nurse is noted to be marginally elevated and his screening blood profile normal. He is told to follow up in the family physician's office in two weeks. On the second visit the patient's blood pressure remains elevated. This brief momentary dual snapshot of information obtained during two separate visits at different times, and under different conditions, is then used by the physician to access and briefly determine a differential diagnosis as to the probable etiology of the patient's High Blood Pressure. Then the physician will initiate what he or she may deem to be an appropriate medication regime, i.e. with an antihypertensive agent three times per day.

Conventional medical treatment and diagnosis therefore leaves much to be desired in terms of efficacy when one is establishing a diagnosis based upon two brief office visits separated by a 14-day interval. Furthermore inefficiency becomes evident, if not obvious, in an antiquated medication delivery system based on a one-size fits all approach (i.e. TID schedule). When in reality, diurnal morning and evening blood pressure spikes may well have caused an inaccurate diagnosis. The troubling consequences of this, include this one-time walk-in patient now on the street, suffering from potentially life-threatening rebound iatrogenic medication induced hypotension.

Embodiments described herein include a medical modeling system or platform, also referred to as the "dynamic Medical Ecosystems Model" (dMEM), that redefines the practice of medicine through proprietary processes of real-time dynamic medicine incorporating nano-sensors. The dMEM creates and applies to individuals a novel real-time health continuum, where generation and application can begin at the moment of birth. The dMEM monitors an individual's health throughout their life. As such, the dMEM provides a virtual platform, creating and enabling preemptive-preventive self-care delivery in real-time. The dMEM along with technological advances in medical nano-sensors will drive the novel medical paradigm, forever changing the scope and practice of human healthcare.

Although the detailed description herein contains many specifics for the purposes of illustration, anyone of ordinary skill in the art will appreciate that many variations and alterations to the following details are within the scope of the embodiments described herein. Thus, the following illustrative embodiments are set forth without any loss of generality to, and without imposing limitations upon, the claimed invention.

Figure 2:
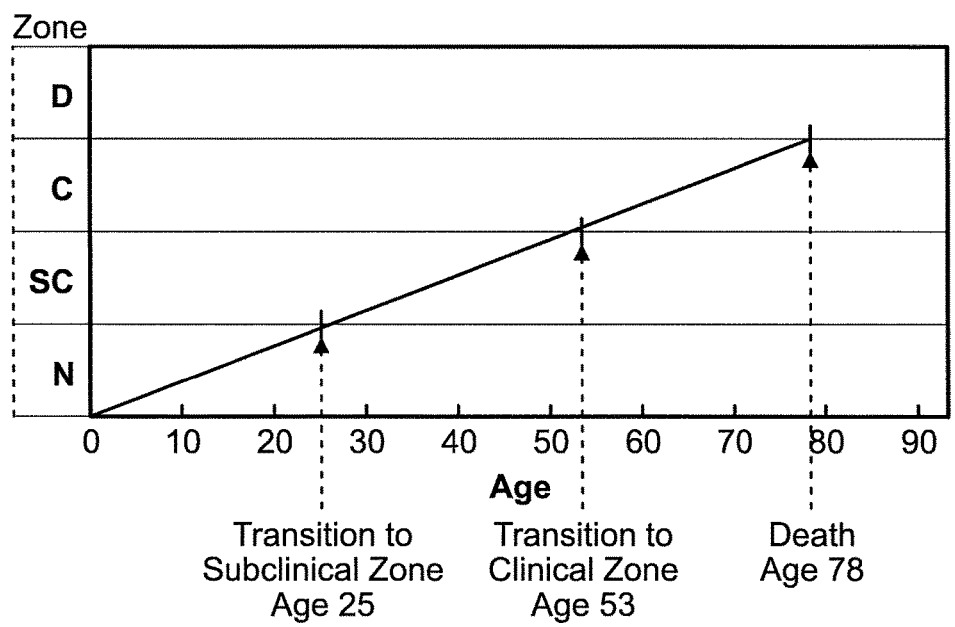
FIG. 2 is a plot of the Life Cycle Line, under an embodiment.

The dMEM of an embodiment develops a Life Cycle Line model, or static life cycle, into a dynamic living model as described in detail herein. FIG. 2 is a plot of the Life Cycle Line, under an embodiment. In essence, a completed (static) Life cycle Line represents the linear graph of an individual's cumulative life, beginning at birth, progressing through normal, subclinical, and clinical zones culminating in death. In the completed cycle, the slope of an individual's Life Cycle Line may have increased or decreased as a result of life choices. The graphic indicates the male in this case, had a relatively disease free life. At the age of 25 he crossed from the normal zone N (no underlying disease process) into the subclinical zone SC (no symptoms to indicate disease, but detectable disease is apparent on labs, imaging studies, etc.; statistically, the majority of the US population enters a subclinical disease zone as early as the third decade with the onset of clinical symptoms by the fifth decade), and by age 53 years a low-grade clinical zone C (disease state arriving to the point of symptom presentation causing the patient to seek medical attention; this is currently the main point of entry into US healthcare by most first-time patients). From age 53 years to 78 years his symptoms, in the clinical zone gradually progressed upwards with death D occurring at 78. The Life Cycle Line ends upon the death of the corresponding individual.

The upward or downward slope of an ongoing dynamic Life Cycle Line determines not just the length of one's life but the quality as well. It is anticipated that much of twenty-first century healthcare will be directed towards assisting individuals in the proper day-to-day data management of his or her dMEM on the dynamic Life Cycle Line model. In doing so, metabolic disease states, both chronic and acute, will be eradicated with marked overall reductions in early life morbidity, disability, and death. It is presently known that well over 45% of progressive acute and chronic metabolic disease states in the U.S. are due to early-learned aberrant behavioral patterns. Learned behavioral patterns are subject to modification and can be positively modified by the dMEM, resulting in dramatic improvements in overall life-long health and wellbeing.

Figure 3:
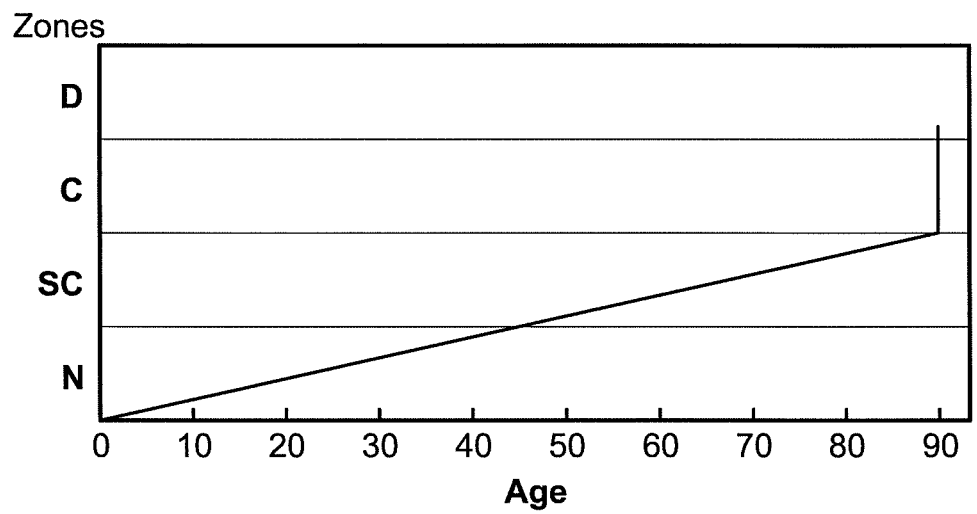
FIG. 3 is a completed graphical representation of a Life Cycle Line of a first individual, under an embodiment.

Detailed examples are presented below to illustrate how the Life Cycle Line may appear in three different people, with three distinct causes of death. FIG. 3 is a completed graphical representation of a Life Cycle Line of a first individual, under an embodiment. The individual of this example has properly cared for their health and wellness, living to an age of 90 years with great quality of life, under an embodiment. Even in an individual who is healthy, the natural course of events range from normal at birth, with varying transitions into sub-clinical and clinical disease prior to death. The 90-year-old individual maintained a great quality of life, without significant lifetime clinical (symptomatic) disease, as per her Life Cycle Line. Although subclinical (asymptomatic) disease was evident from the age of 45 years until the time of her demise, death in this case occurred due to an unexpected head-trauma from a fall resulting in a massive hemorrhagic stoke.

Figure 4:
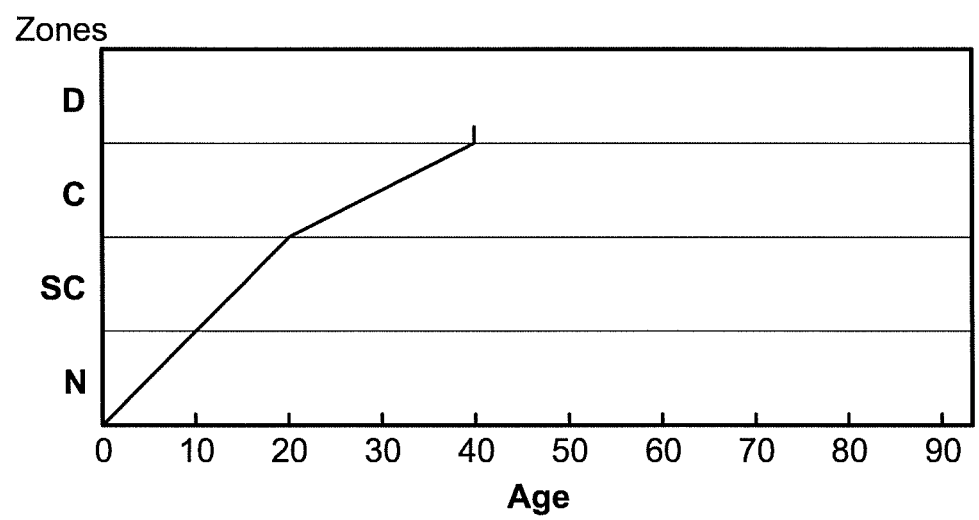
FIG. 4 is a completed graphical representation (post-mortem) of morbid childhood obesity and poor impulse control that has a snowballing effect on the individual's health and wellness, under an embodiment.

FIG. 4 is a completed graphical representation (post-mortem) of morbid childhood obesity and poor impulse control that has a snowballing effect on the individual's health and wellness, under an embodiment. At age ten years, the individual crosses into the subclinical zone (elevated blood sugars), eventually crossing into the clinical zone by age 20 with adult onset insulin dependent diabetes. The ability to directly quantify a person's everyday actions into one output is a key concept in the Life Cycle Line.

Figure 5:
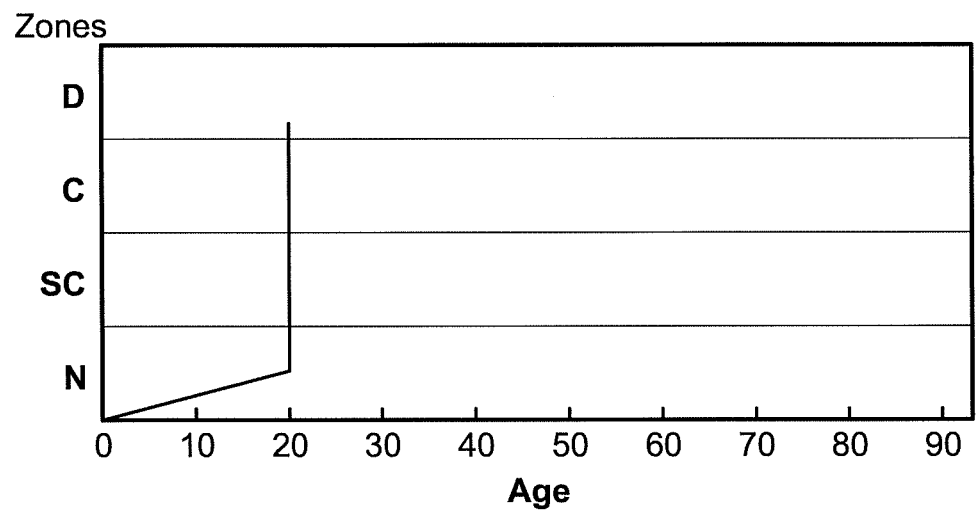
FIG. 5 is a completed graphical representation of a Life Cycle Line where the individual is in the normal zone, and was subject to random environmental factors, under an embodiment.

FIG. 5 is a completed graphical representation of a Life Cycle Line where the individual is in the normal zone, and was subject to random environmental factors, under an embodiment. His Life Cycle Line went from the normal zone vertically through subclinical and clinical zones into death. He was a healthy twenty-year old who was originally projected to live for at least 83 years. This individual's life was cut drastically short, killed in action in Afghanistan at age 20.

Figure 6:
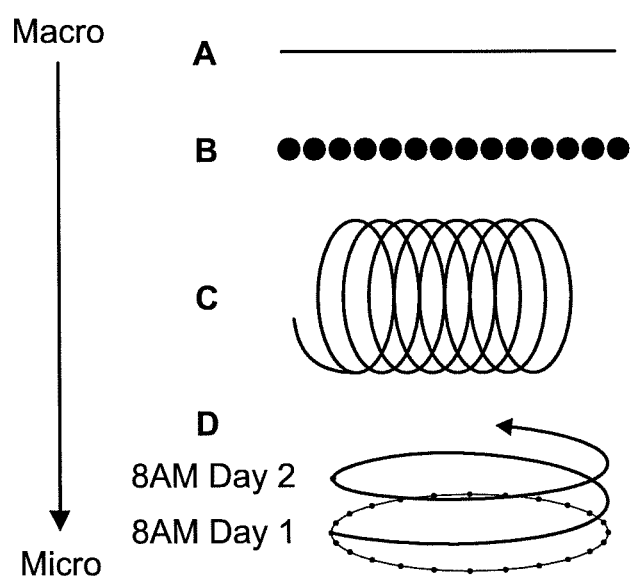
FIG. 6 is a block diagram showing development of the dynamic Medical Ecosystems Model (dMEM), under an embodiment.

Consideration of the linear graphical components described herein provides context for the more complex underlying processes of the dMEM of an embodiment. For the sake of the description herein, the following example will employ a hundred year life. FIG. 6 is a block diagram showing development of the dMEM, under an embodiment. A hundred years on the sloping lifeline in this model will equal 36,500 days of life, representing a single Life Cycle Line A (continuous uninterrupted life cycle line) of 36,500 connecting points B (composite points that comprise continuous line A). Hence a single point on the Life Cycle Line represents one day or a completed 24-hour cycle, which equates to a 360-degree circle. It is upon this circle the nano-monitored events or physiological data of the previous 24-hour period is recorded and analyzed. The 24-hour event cycle is in reality a continuous helix in the dMEM process as described in detail herein. It returns to the same beginning point every 24 hours, but due to the passing of time it is located at a slightly different point in space.

Figure 7:
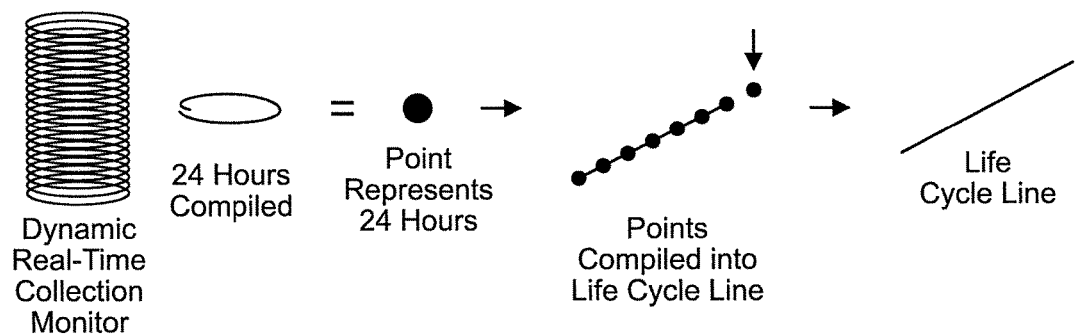
FIG. 7 shows a flow diagram of Life Cycle Line development, under an embodiment.

With reference to FIG. 6, the basis for the dMEM process model or computer model arises from C (each completed cycle on the helix represents a composite point on B) and D (each mapped 24-hour cycle (e.g., 8 am to 8 am) represents a composite revolution on C) in the diagram showing dMEM development. The dMEM of an embodiment includes a 24-hour cycling processor-based (e.g., server, cloud, personal computer, etc.) platform that collects real-time multiples of physiologic data from medical micro sensors (external or internal), while using the cyclic models of C and D, to essentially change the Life Cycle Line from a static to a dynamic entity. The helical recordings of each 24-hour cycle maintain all medical data corresponding to an individual. Daily 24-hour cyclic recordings can then be plotted to a patient's Life Cycle Line. FIG. 7 shows a flow diagram of Life Cycle Line development, under an embodiment.

More particularly, the dMEM receives physiological data that includes data of multiple physiological parameters collected in real-time from sensors coupled to an individual subject. The sensors are coupled to or implanted in the subject, and are configured to telemeter the physiological data to the dMEM platform or otherwise offload or download the physiological data to the dMEM platform. The sensors of an embodiment include sensors of any type and/or configuration as appropriate to collection of physiological data from a living entity. Furthermore, the physiological data includes any data or parameters capable of being collected from a human subject.

Upon receiving the physiological data, the dMEM generates a number of micro plots, where each micro plot represents or corresponds to a particular time period. Each micro plot includes a cyclical plot of the physiological data for a corresponding time period (e.g., 24-hour period, etc.). Thus, each micro plot comprises an integrated plot of all physiological data collected from a subject during the corresponding time period. Using the micro plots, the dMEM generates a medical model plot, or Life Cycle Line. In generating the medical model plot, the dMEM plots the micro plots chronologically according to the corresponding time periods, such that a location of an endpoint of each micro plot determines a change in slope of the medical model plot. As described in detail herein, the slope of the medical model plot represents a state of health of the human subject.

The successful dMEM from 0 to 90 years equals a connected series of 32,850 points representative of a continuum of days. Furthermore, each point may then be reduced to a non-random reoccurring 24-hour cycle that essentially returns to the same position after completion of a 360° rotation over 24 hours. Each hour represents 1/788,400$^{th}$ of 90 years and equates to 15° rotation on each 360° cycle. Each rotation returns to the same point in the 360° rotation but has moved in space to a new position representing the end of one 24-hour cycle and the beginning of a new 24-hour cycle. Hence the dMEM exists as a helical entity in space.

Figure 8:
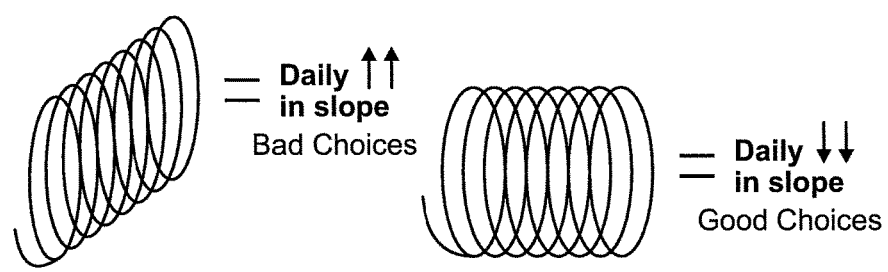
FIG. 8 shows slope changes in the dMEM, under an embodiment.

The point in space that ends each monitored cycle, determines the change of slope in the dMEM. This slope change correlates to the actions and behaviors of the preceding 24-hour cycle. The dMEM precisely displays changes in an individual's monitored actions and choices for the upcoming day, based upon the choices made the day before. FIG. 8 shows slope changes in the dMEM, under an embodiment. Representative drivers for an increased slope (less time in the normal zone, shorter life, worse quality of life) include, but are not limited to, the following: aberrant behavioral patterns; excessive alcohol consumption; unhealthy, unbalanced diet; tobacco use; sedentary lifestyle; depression; low education levels; living at or below the poverty level. Representative drivers for a decreased slope (more time in normal range, longer life, better quality of life) include, but are not limited to, the following: no alcohol consumption; healthy balanced caloric diet; no tobacco use; active lifestyle; good mental hygiene; higher education levels; living above poverty level.

Therefore, the plotting of each 24-hour cycle of monitored physical and metabolic parameters and changes produces a continuous helix representing the true dynamic nature of the dMEM. By dissecting the helix, each previous and succeeding monitored cycle can be directly compared with others. For example, once a baseline of seven consecutive cycles is obtained, these may be sequentially compressed to a single cycle, yielding a weekly compilation. Uniform compression of a month, year, or decade becomes possible as aging data becomes available for compression. The end-user will have multi-sourced feedback available continuously.

Figure 9:
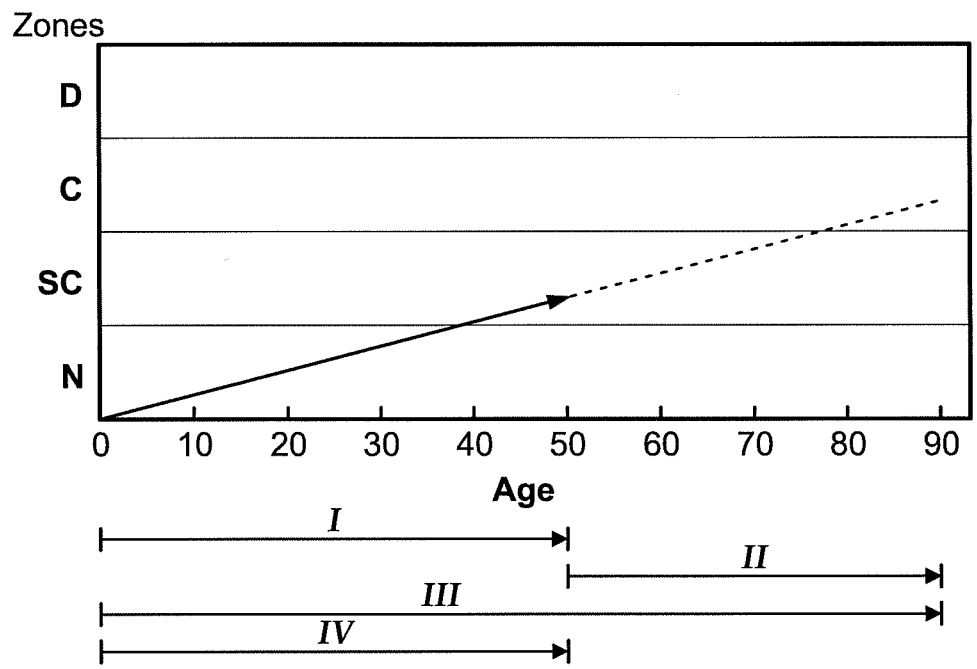
FIG. 9 shows the dynamic Life Cycle Line, under an embodiment.

New medical paradigms are emerging of which the dMEM will be a major component. For example, a first medical paradigm is one in which preemptive "self-healthcare" will virtually eradicate acute and chronic disease states. A second medical paradigm is one that reveals previously undiagnosed disease, significantly augmenting future medical and surgical outcomes. A third medical paradigm is one in which future dynamic medical, biomedical, pharmacological, academic, and epidemiologic research and stratification, changes the face of global health. A fourth medical paradigm is one in which supercomputers, physiology, and medicine become a singular dynamic real-time continuum. FIG. 9 shows the dynamic Life Cycle Line, under an embodiment. The Life Cycle Line demonstrates the future point of entry, integration, and flow of the emerging paradigms (I, II, III, IV) in the healthcare continuum. A detailed description of the new medical paradigms follows.

Figure 10:
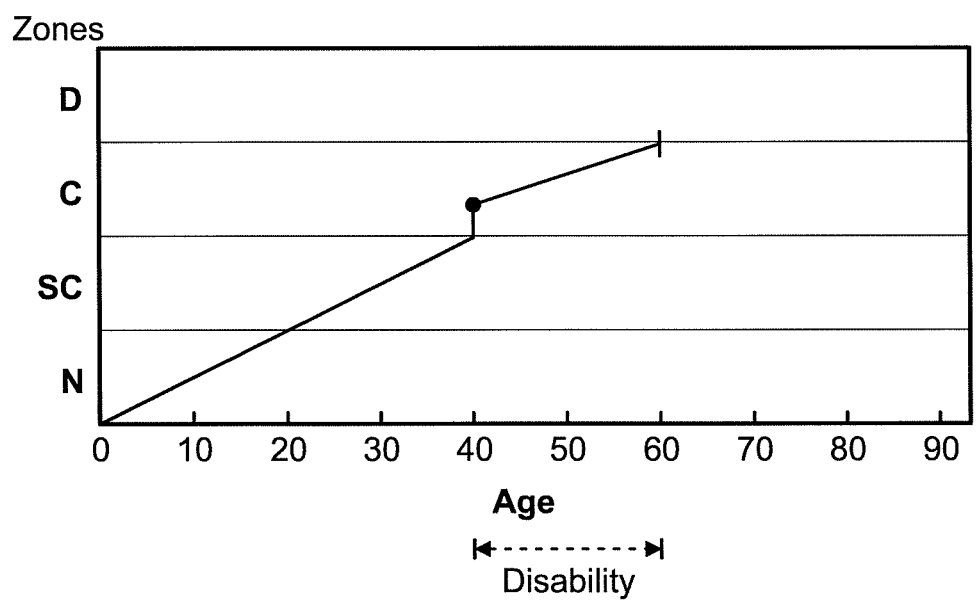
FIG. 10 shows a plot of a Life Cycle Line depicting an individual who did not incorporate any kind of health monitoring into their lives, an Unmonitored Lifestyle, under an embodiment.

With reference to the first new medical paradigm, an example of the dMEM as a preemptive "self-healthcare" model can be demonstrated by comparison of the following completed Life Cycle Lines. The dMEM of an embodiment virtually eradicates acute and chronic disease states. FIG. 10 shows a plot of a Life Cycle Line depicting an individual who did not incorporate any kind of health monitoring into their lives, an Unmonitored Lifestyle, under an embodiment. Thus, they did not have feedback regarding how their day-to-day choices truly impacted their future health and longevity. This individual suffered from a massive heart attack at age 40 years due to his aberrant behavioral patterns. He survived the event, but as noted in the Life Cycle Line, from age 40 years until death at age 60 years, the patient remained permanently and totally disabled, dependent upon government resources.

Figure 11:
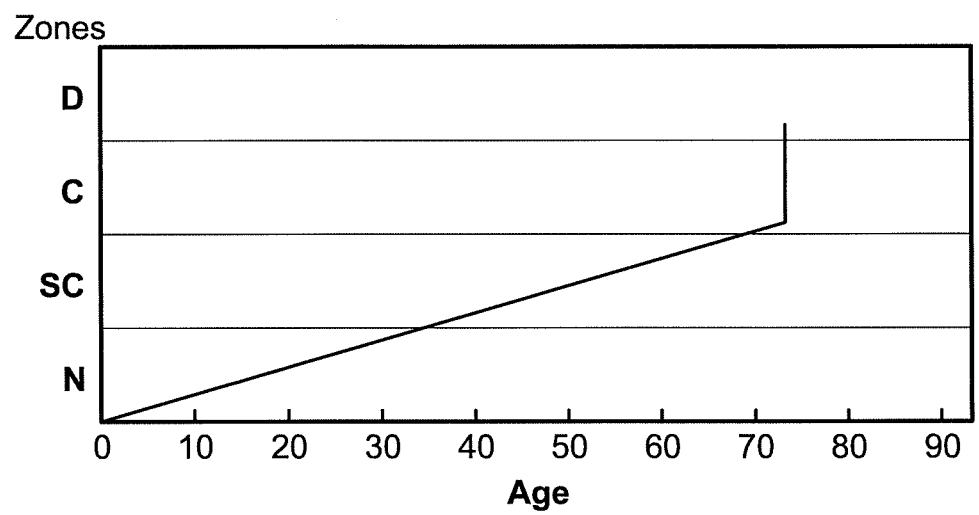
FIG. 11 shows a plot of a Life Cycle Line depicting a Monitored Lifestyle, under an embodiment.

FIG. 11 shows a plot of a Life Cycle Line depicting a Monitored Lifestyle, under an embodiment. This individual's health was monitored from age 10 years. The data collected continuously from the individual was processed via the dMEM to yield his Life Cycle Line. From the time this individual was a child, he and his parents had the benefit of knowing how his (and his parents') choices were impacting him. The child would learn from a much earlier age which choices in his life are truly healthy. The visual feedback from the Life Cycle Line would provide positive reinforcement for healthful living from a very young age. This preemptive "self-healthcare" would necessarily eliminate 45% of debilitating acute and chronic metabolic disease states in the U.S. Healthcare dollar savings would be tremendous. With the Monitored Lifestyle, the patient was able to see an improved quality of life, improved longevity, and productive lifestyle with absence of disability, until death at 74.

Under the second new medical paradigm, in the diagnosis and treatment of existing acute and chronic disease states, a shift occurs from preemptive preventive medicine, to one of treatment of established disease, as osteoarthritis, rheumatoid arthritis, carpal tunnel syndrome, and cervical radiculopathy are explored.

Figure 12:
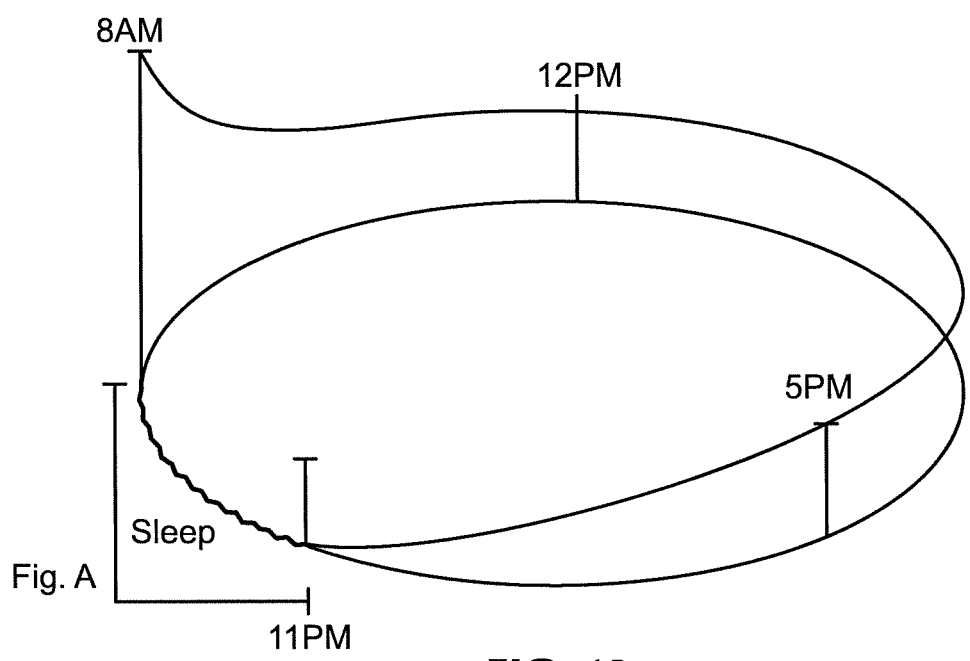
FIG. 12 is an example dMEM recording of the first patient, under an embodiment.

In a first example under the second new medical paradigm, two 60-year-old male patients, new to the doctor's office on the same day, complain of generalized aches and pains consistent with arthritis. The tendency is to treat them medically based on a "snapshot moment in time" office visit. In this case they both would likely be treated symptomatically with anti-inflammatory medication and sent home. When the monitored cyclic dMEM is applied on a real-time 24-hour cycle for seven days and then compressed, two distinctly different patterns of pain begin to emerge. The first patient would elicit a pattern analogous to rheumatoid arthritis with progressive pain at its zenith in the early morning hours, as seen in the patient's dMEM recording. FIG. 12 is an example dMEM recording of the first patient, under an embodiment.

Figure 13:
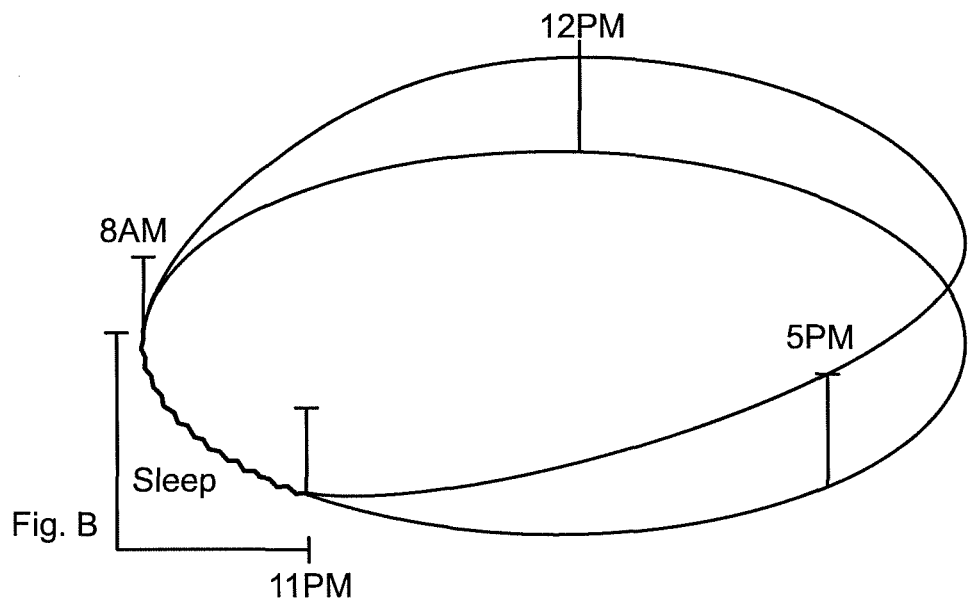
FIG. 13 is an example dMEM recording of the second patient, under an embodiment.

The second patient's pain pattern will demonstrate its true zenith in the mid afternoon, which would indicate degenerative arthritis, as seen in the patient's dMEM recording. FIG. 13 is an example dMEM recording of the second patient, under an embodiment. This becomes apparent in the real-time recurrent cycling "movie" while not recognized nor likely considered by modern day "snapshot" medicine. Both patients are misdiagnosed as a result, and neither receives accurate or appropriate care.

The relative differences seen between the dMEM recording of the seven-day compressed data compilation (FIG. 12) of a pain pattern in the first patient with rheumatoid arthritis, and the dMEM recording of the seven-day compressed data compilation (FIG. 13) of a pain pattern of the second patient with degenerative arthritis shows that the treatments for active rheumatoid arthritis are vastly different than the prescription for anti-inflammatories the patient was given. With the use of dMEM monitoring, the previously unseen physician errors, misdiagnoses, and inappropriate treatments are quickly revealed.

Figure 14:
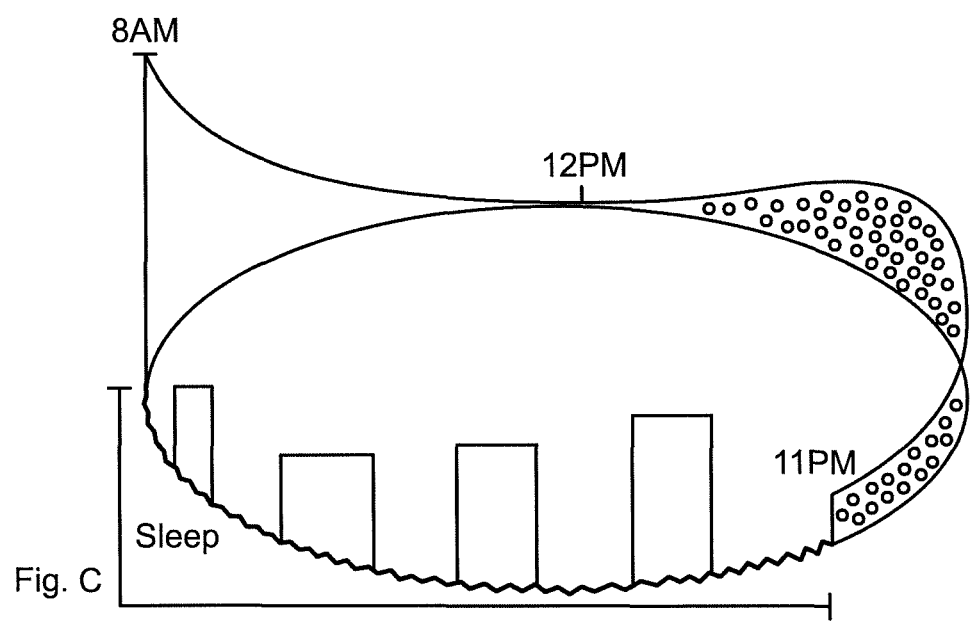
FIG. 14 shows the dMEM recording of the previous seven-day compressed data compilation of this patient's pain pattern, under an embodiment.

A 45-year-old patient presenting with radiating neck, arm, and hand pain represents a second example under the second new medical paradigm. He was recently involved in a motor vehicle accident (MVA) and has cervical radiculopathy, and is currently awaiting C-spine surgery in five days, as recommended by his neurosurgeon. The patient worked as a diesel mechanic, and had well documented pre-existing occasional hand pain radiating into digits 1, 2, 3, and forearm prior to the MVA. He now has severe hand pain running into digits 1, 2, 3, with forearm, arm, and neck pain. FIG. 14 shows the dMEM recording of the previous seven-day compressed data compilation of this patient's pain pattern, under an embodiment. The pain clearly varies during course of the day. The dotted elevation in pain is denoted as primarily sharp neck, shoulder, and forearm pain radiating into the hand. The solid red markers indicate dull pain occurring primarily in the hand and forearm.

The pain diagram, to an astute clinician using the dMEM, will be obvious and can be easily compared to stored database renderings to confirm the diagnosis, with a probability nearing one. The patient, in reality, has pre-existing low-grade carpel tunnel syndrome that is now acute secondary to the double crush from MVA induced acute cervical radiculopathy. The patient has two diagnoses and will need two surgeries: a C-spine surgery and carpel tunnel release before he will get total relief.

Figure 15:
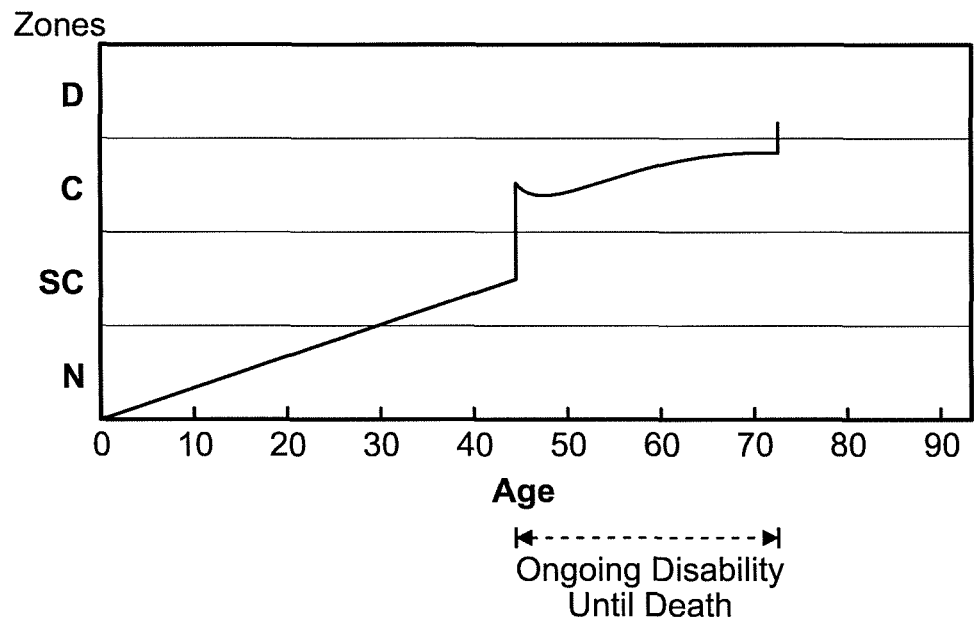
FIG. 15 is a plot of the cure rate of the patient having only C-spine surgery, under an embodiment.

Without the dynamic dMEM compressions he would have likely been diagnosed and treated with C-spine surgery only. His cure rate would have been reduced to 33% with chronic pain and ongoing disability until death. FIG. 15 is a plot of the cure rate of the patient having only C-spine surgery, under an embodiment.

Figure 16:
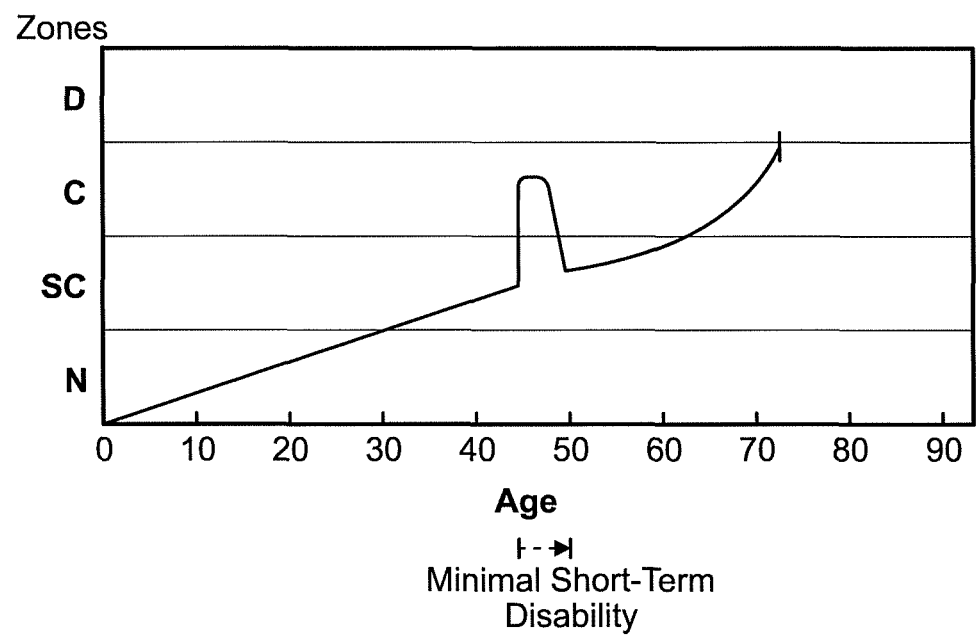
FIG. 16 is a plot of the cure rate of the patient having C-spine and carpel tunnel release surgeries, under an embodiment.

If both diagnoses had been made and both surgeries performed, his cure rate would have been 85%, with minimal short-term disability. FIG. 16 is a plot of the cure rate of the patient having C-spine and carpel tunnel release surgeries, under an embodiment.

Figure 17:
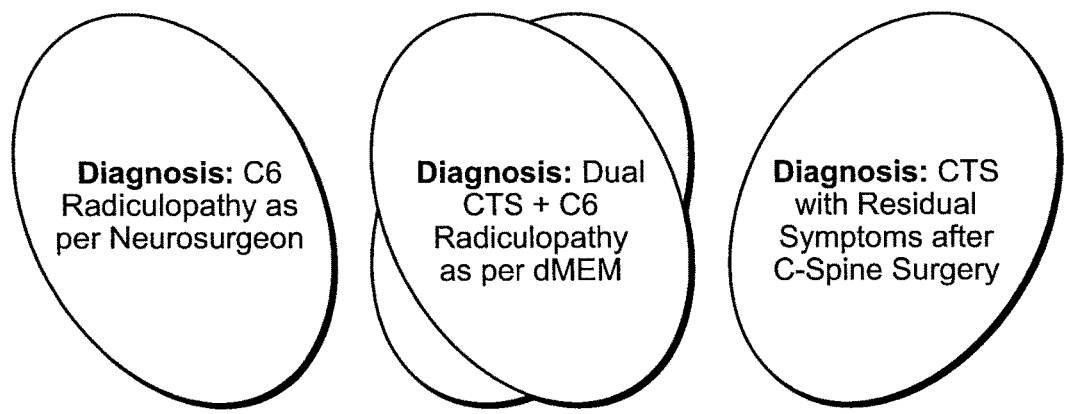
FIG. 17 depicts the superimposed similarity between the pain from carpal tunnel syndrome (CTS), and recent onset cervical radiculopathy, under an embodiment.

FIG. 17 depicts the superimposed similarity between the pain from carpal tunnel syndrome (CTS) (right-tilted oval), and recent onset cervical radiculopathy (C6) (left-tilted oval), under an embodiment. The C6 oval illustrates the treating physician's assumed single diagnosis based on MRI changes consistent with cervical radiculopathy, but further assessment via dMEM compressions would have clearly revealed a dual overlapping diagnosis (crossed ovals) of cervical radiculopathy C6 and secondary carpel tunnel syndrome (CTS), creating a double crush phenomenon.

Figure 18:
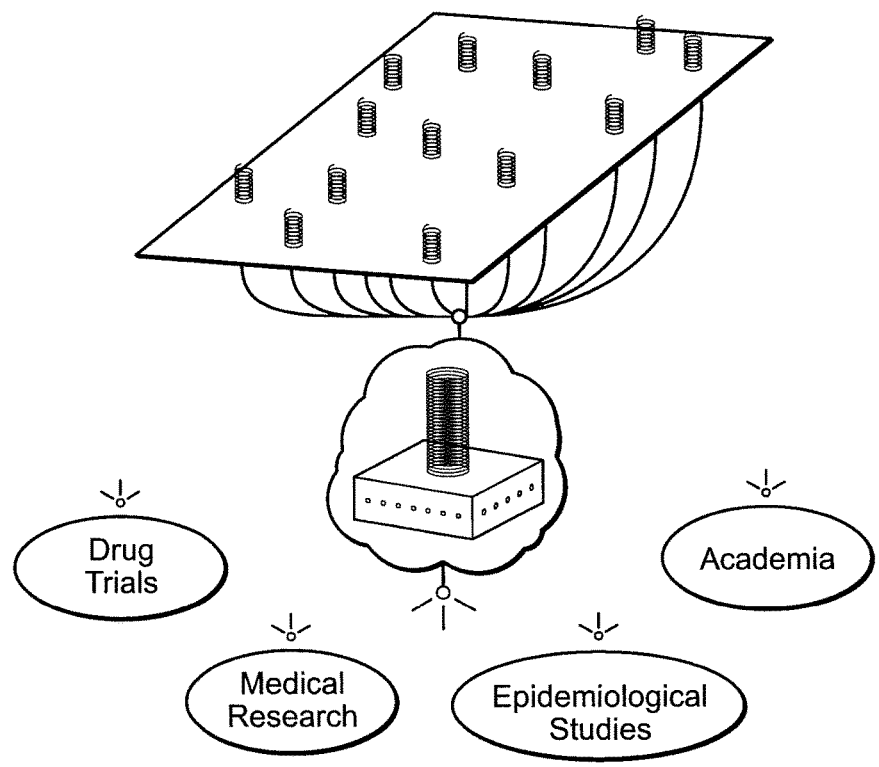
FIG. 18 illustrates multiple end users linked to the dMEM cloud, under an embodiment.

Referring to the third new medical paradigm, FIG. 18 illustrates multiple end users linked to the dMEM cloud, under an embodiment. This allows for scalable real-time data acquisition. Multiple end user institutions (medical, academic, among others) under this embodiment select from a number of parameters they wish to monitor or study in real-time. For example, in the diagram below, the hypothetical plane may represent an institution's selected area of current study. This could include geographical distribution, age distribution, race distribution, disease prevalence, etc. All of these parameters and more are monitored in real time using the dMEM.

Drug companies, for example, will use the dMEM to monitor multiple cohorts of study participants in ongoing real-time clinical trials. This will undoubtedly change the dynamic of clinical drug trials with the earliest yet recognition of a drug's efficacy, safety, as well as unanticipated positive or negative collateral side effects.

Figure 19:
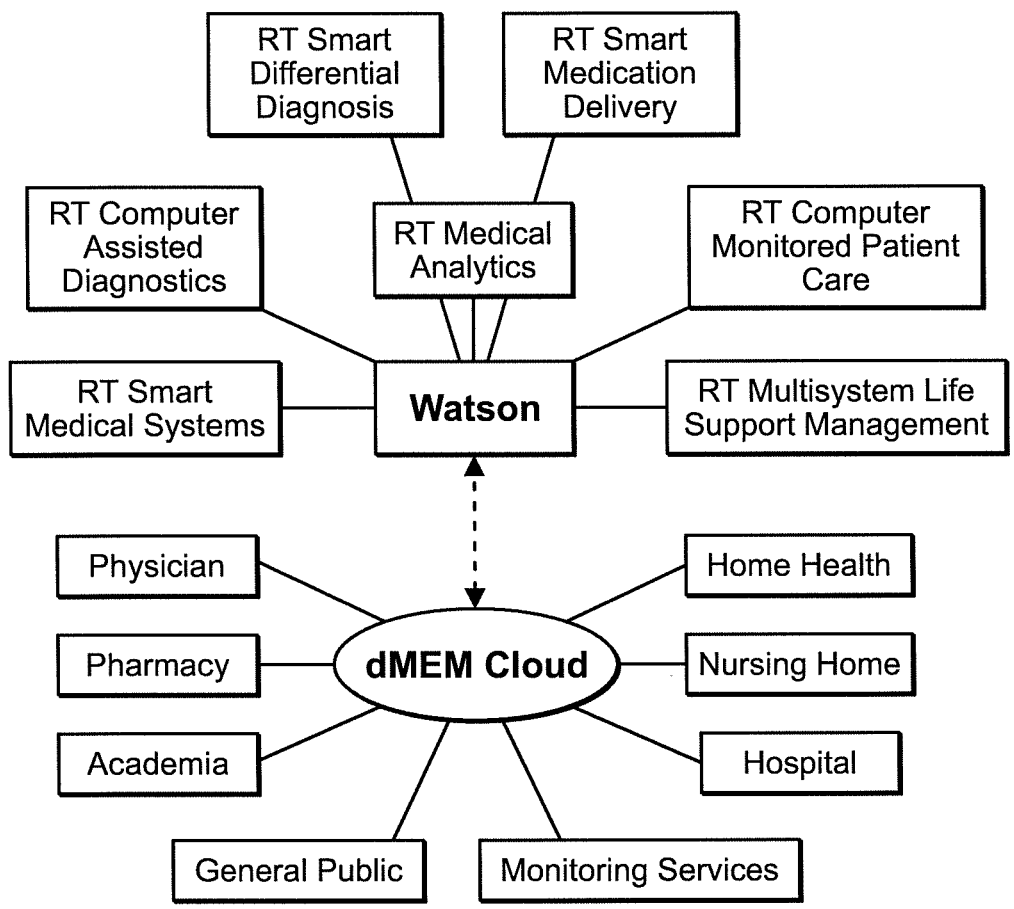
FIG. 19 is a block diagram of the dMEM integrated with a supercomputer system, under an embodiment.

Referring to the fourth new medical paradigm, the integration of a supercomputer system into the dMEM ensures that every individual, patient, hospital, and medical institution in the world will have a continuous open-ended flow of real-time input and data collection from global supercomputer guided diagnostics and treatment. FIG. 19 is a block diagram of the dMEM integrated with a supercomputer system, under an embodiment.

In the past three decades, U.S. Healthcare has experienced exponential technological growth in "linear" diagnostic imaging and treatment systems. These advances have consistently been directed and ultimately designed to assess and or treat established pre-existing acute and chronic disease states, often as design-specific "post-event" diagnostic and treatment modalities i.e. heart, stroke, cancer care, etc.

For this reason, all diagnostics developed and introduced in the past thirty years tend to cluster around the after-the-fact points of clinical presentation due to chronic dysfunctional and acute event occurrence (heart attack). No significant preventive measures of any kind have been able to change the paradigm to this point in time. During this same thirty-year period, the medical dollar spent on design and development of preemptive preventable disease management lagged far behind. This was particularly true for the concept of medical ecosystems development until recent advancements in medical nano-sensors established a real and present niche-need. Nevertheless, it is calculated that a rapid paradigm shift to multi-dimensional medical ecosystem will significantly impact the anticipated growth curve in "linear" healthcare research and development over the next two decades. This will be particularly evident as the scalable medical ecosystems of the dMEM provide and guide individual health and healthcare delivery on a real-time 'day to day' basis by the application of its preemptive medical capabilities.

The state of medical nanotechnology is evolving rapidly, and the multiplicity of nano-sensor and sensor derivatives expected to enter the market over the course of the next five years will see exponential growth in numbers. Diversity of development, sensitivity and continued diminution in size will ensure that an expanding array of disparate technical and medical applications will continually be available to the mobile general public. However, in the coming years as industry maturity occurs, the surviving spectrum of segmented medical apps will be forced to unify and standardize across the board before nanotechnology as a emerging field in medicine may flourish.

The conventional novelty applications running at any one time measuring an individual's vital signs may suffice for the younger health-oriented segment of society. These applications, or apps, can be configured to continuously monitor for a "triggering event" such as an irregular heartbeat while an end-user is exercising. At that point where the anomaly is sensed, the data capture on the end user can increase, by initiating other apps (e.g., an app for cardiac enzymes) to monitor associated parameters.

That said, to become a fully integrated adjunct in the future of both preemptive-preventive and acute critical care medicine, the systems of the dMEM of an embodiment are configured to run and monitor 60 to 200 and more integrated real-time apps on an ongoing 24/7 basis. As a result, the dMEM makes use of a mammoth data collection-compression architecture with sensitivity extending well beyond linear and planar mappings of 24 hours. The computing hardware, storage and bandwidth for such an endeavor is readily available with cloud-based web-services and datacenters offered by third party providers. The limiting factors will not be computer or hardware capacities, but rather innovative configuration and integration. Medical nano-sensors combined with the dimensionality of real-time human physiology will push present computing architectures into a multi-dimensional framework.

Figure 20:
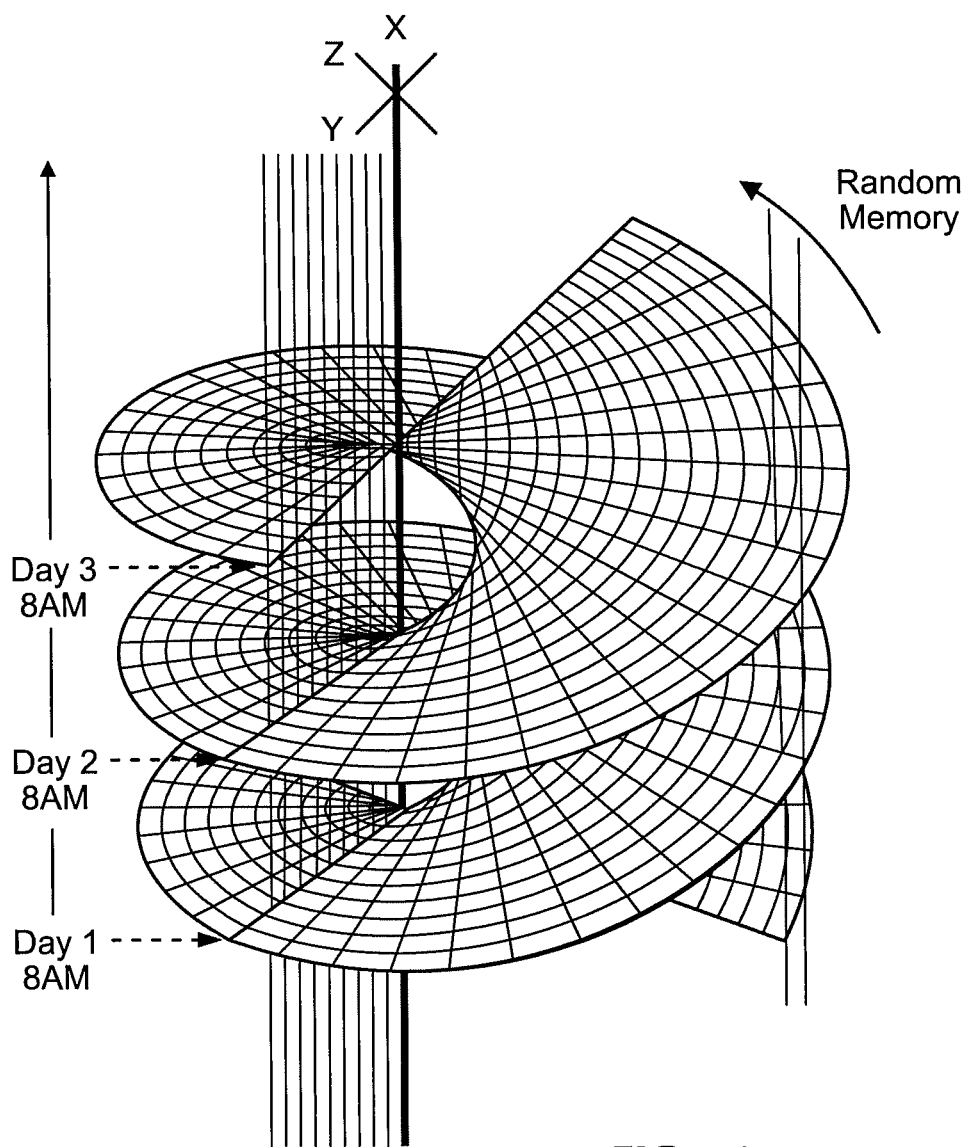
FIG. 20 depicts a helicoid example underlying the dMEM system design, under an embodiment.

Since the beginning of time, intelligent life on earth has been dependent and unknowingly subservient to cyclic patterns (daily, monthly, yearly). The most obvious of these patterns is the 24-hour circadian cycle, established by earth's rotation. This perpetually reoccurring 24-hour cycle has had countless millions of years programming human life to respond and thrive upon a cycled existence. FIG. 20 depicts a helicoid example underlying the dMEM system design, under an embodiment.

Figure 21:
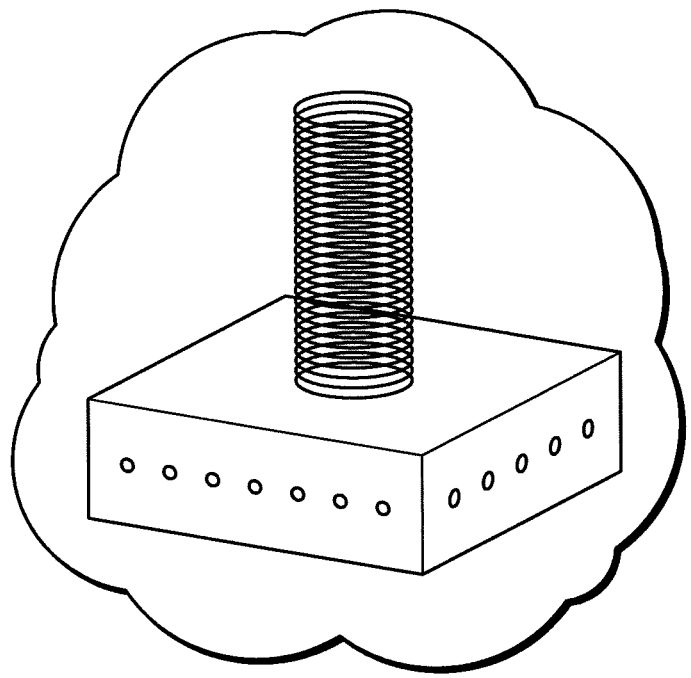
FIG. 21 is a block diagram depicting a dMEMs platform hosting the circadian model, under an embodiment.

The architecture and running system of embodiments described herein give much attention and consideration to a three-dimensional (3D) composite world, to run parallel with real-time physiologic data capture in conjunction with person place time and event. FIG. 21 is a block diagram depicting a dMEMs platform hosting the circadian model, under an embodiment.

Figure 22:
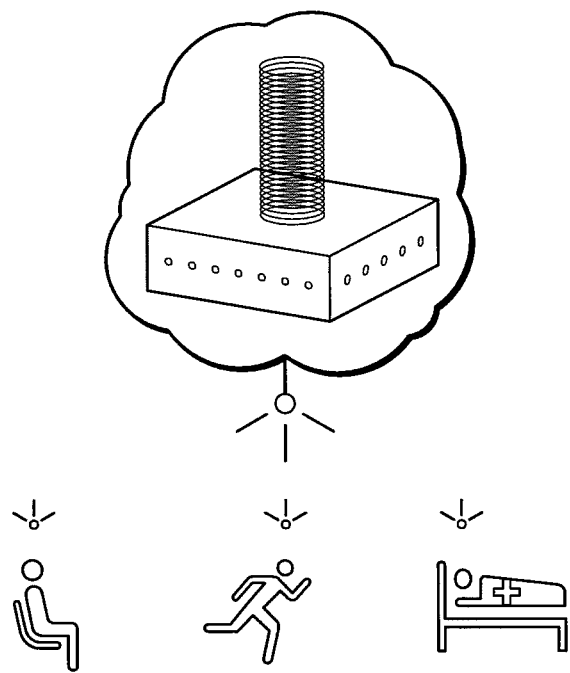
FIG. 22 is a block diagram depicting the dMEMs platform creating a real-time sensing and collecting system running in parallel to human physiology, under an embodiment.

A cloud driven helical architecture is a paradigm changer for the future of medicine. FIG. 22 is a block diagram depicting the dMEMs platform creating a real-time sensing and collecting system running in parallel to human physiology, under an embodiment. Standardization of pre-configured plug and play ports to the cloud platform, the nano-sensor hardware developer need only configure sensor software to interface with the cloud's ports. Each medical nano-sensor developer and their respective software engineers will be provided hands-on tutorials and technical assistance to grasp a thorough understanding of the 3D real-time architecture and the 24/7 operating systems requirements.

Figure 23:
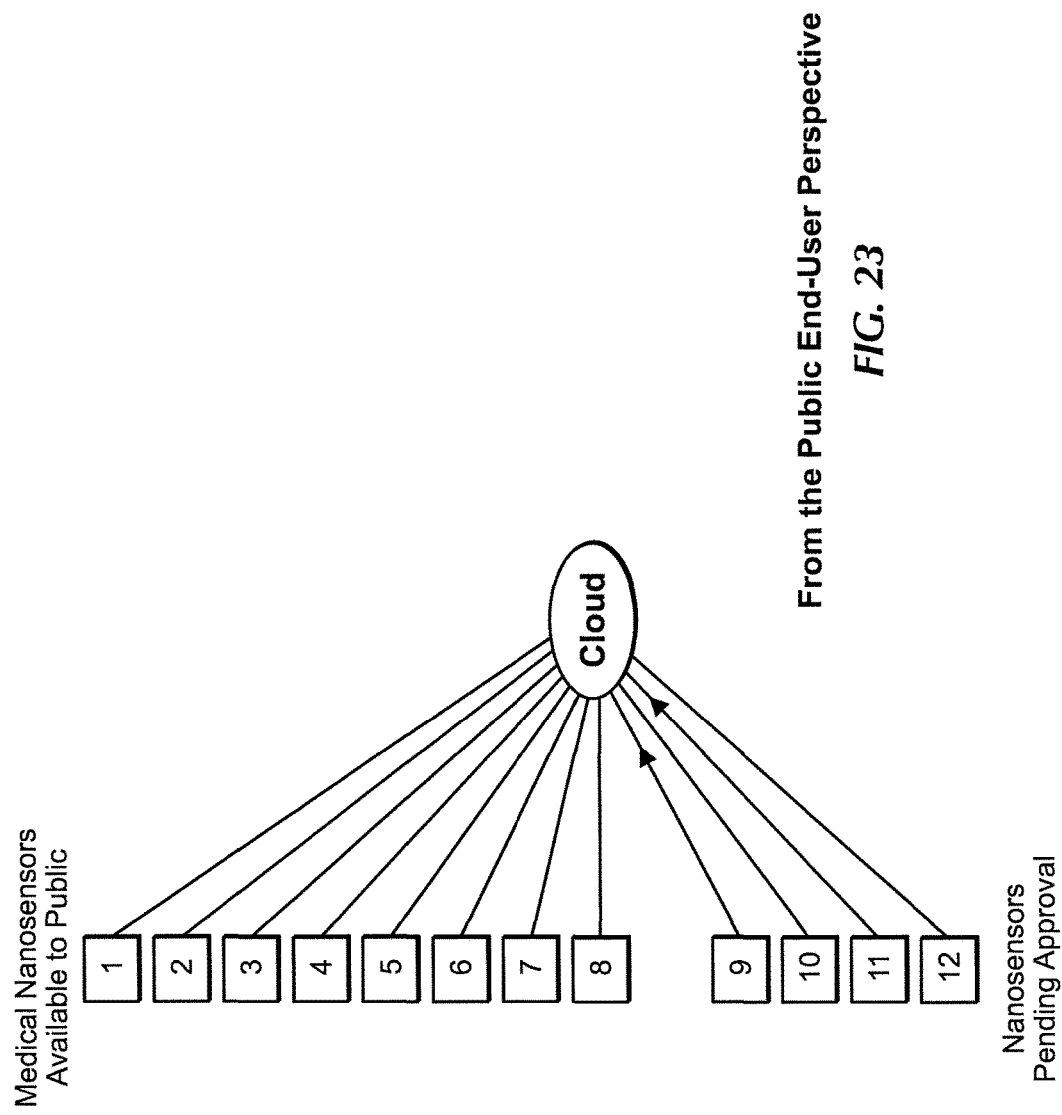
FIG. 23 shows the dMEMs from the perspective of the application/nano-sensor developer, under an embodiment.

FIG. 23 shows the dMEMs from the perspective of the application/nano-sensor developer, under an embodiment. Approaching the embodiments described herein from the perspective of the application/nano-sensor developer, when the app/nano-sensor is approved and selected for port to real-time system migration, the accompanying nano-sensor/app becomes available on the cloud platform to be downloaded and applied to the end users handheld or tablet device. Each app/nano-sensor will be dormant on the cloud until an end-users interface is activated and usage begins.

Figure 24:
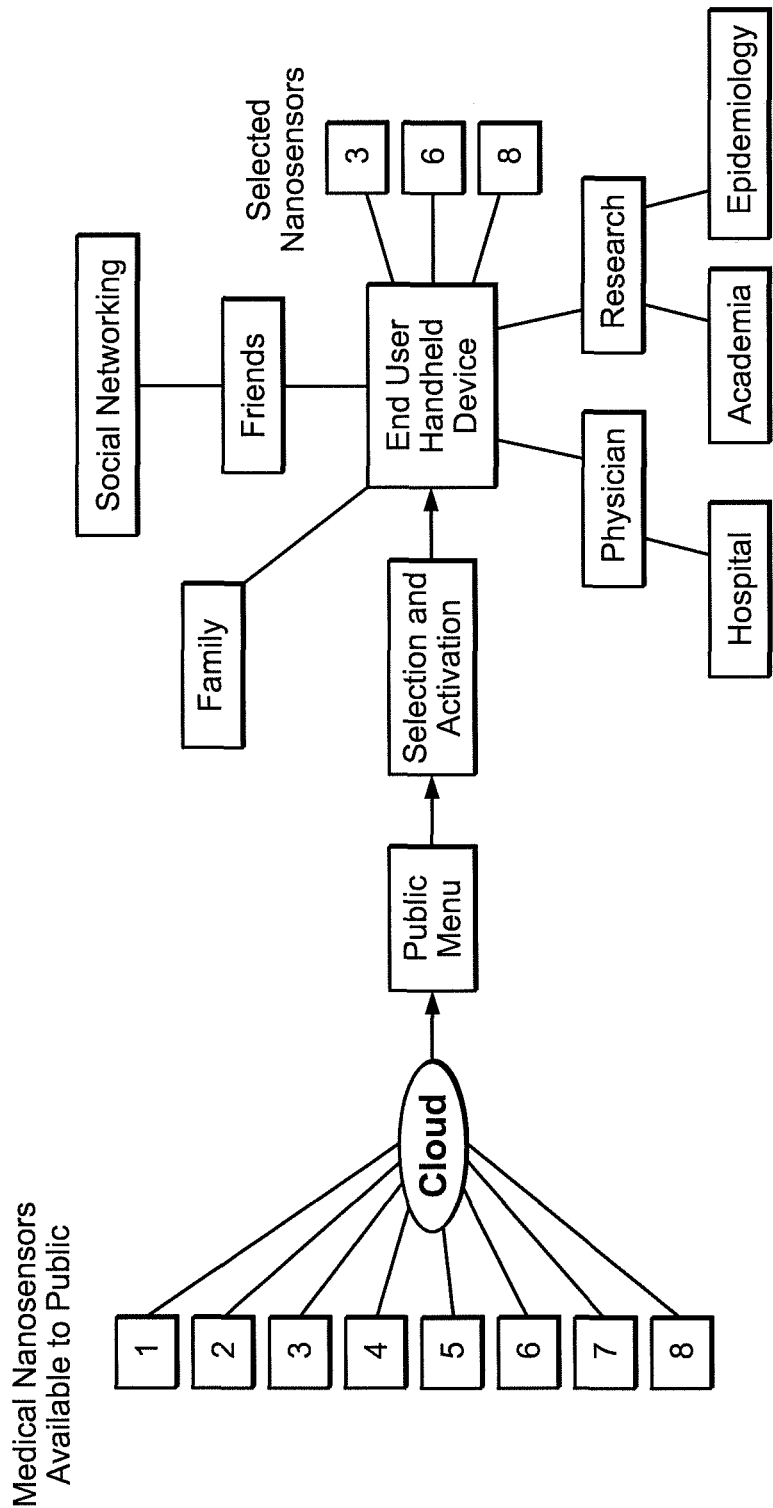
FIG. 24 shows the dMEMs from the perspective of the public end-user, under an embodiment.

FIG. 24 shows the dMEMs from the perspective of the public end-user, under an embodiment. Approaching the embodiments described herein from the perspective of the public end-user, when a new cloud account in opened by an individual, he or she may then, depending upon credentialing be given access to select from approved app/nano-sensor that may be appropriate for public usage. These will be listed on the cloud-based open public interface, much like an app store. Each app will provide a detailed medically oriented description of available usage for the potential end-user, as well as bundling capabilities, bandwidth needs, ordering instructions for hardware, cloud fees, etc. The site owner may also select to provide viewing rights to other family members, various care providers such as physicians, nurses, home health providers, emergency services providers, hospitals and research institutions, etc. Categories of public self-tracking users include the young health conscious adult who wants daily tracking of basic vital health systems linked and plotted to the Life Cycle Line. Monitored users as a category, may be nursing home patients tethered to family physician, hospital, home health, family members, as well as yet to be created general and specialty monitoring systems.

Figure 25:
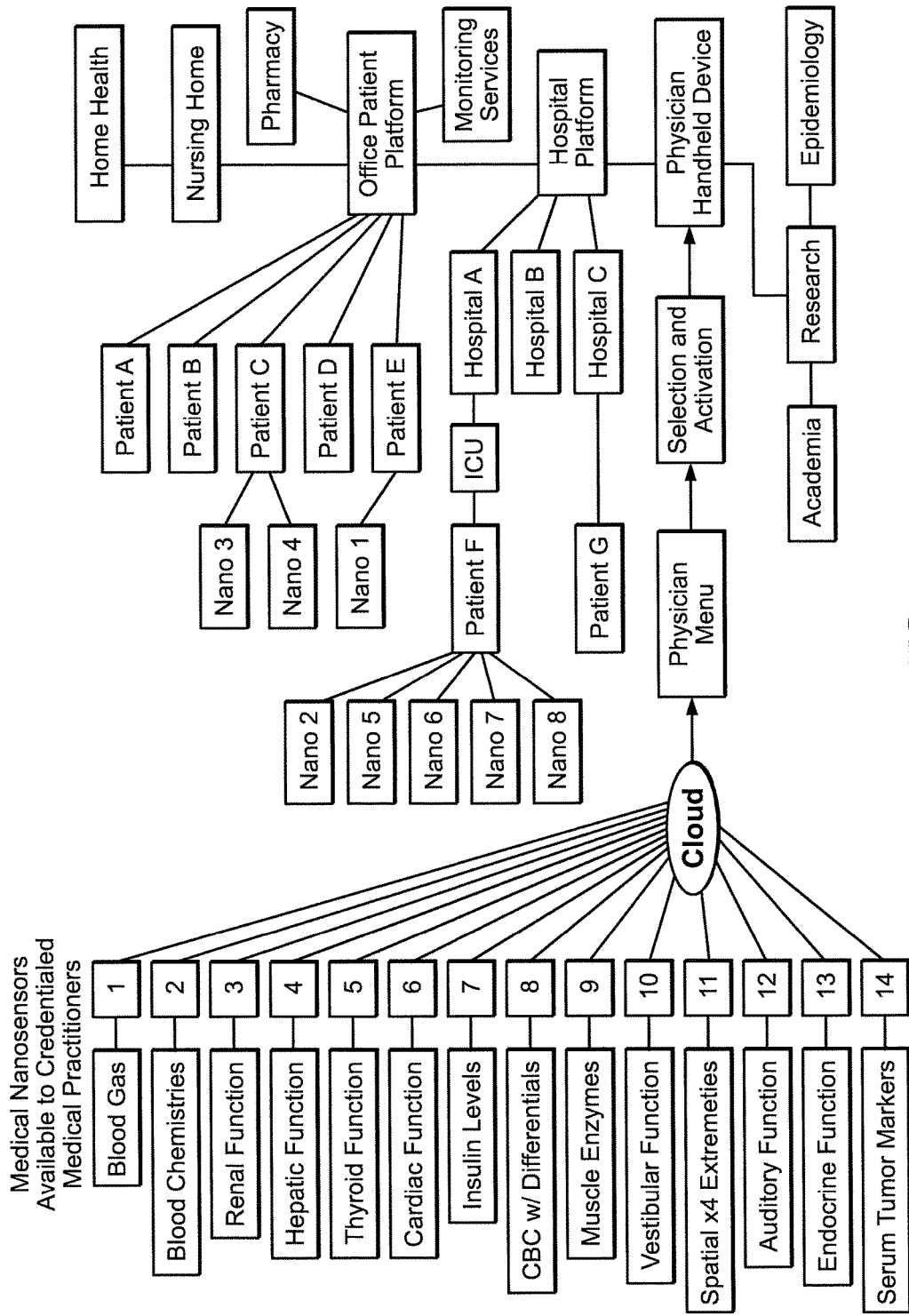
FIG. 25 shows the dMEMs from the perspective of the active practice physician, under an embodiment.

FIG. 25 shows the dMEMs from the perspective of the active practice physician, under an embodiment. Approaching the embodiments described herein from the perspective of the active practice physician, when a new account is opened in his or her name and credential verification has occurred the physician is given direct access to appropriate (non-public) medical apps commensurate to his/her specialty and training. He or she will be able to potentially link-in to his patient's existing user site and add medically monitored sensors that extend beyond normal public access.

Figure 26:
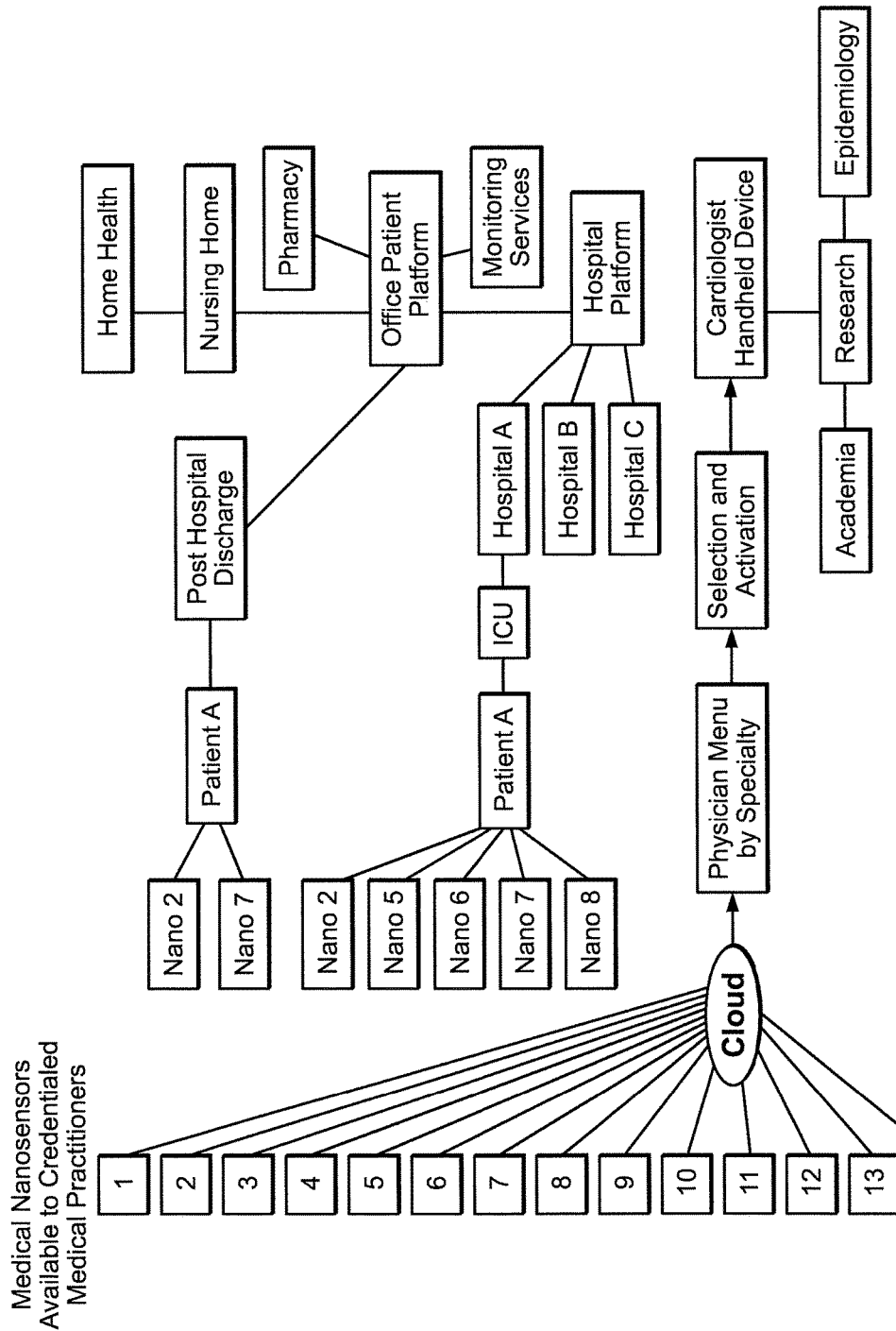
FIG. 26 shows an example of the dMEMs from the perspective of the active practice physician when treating a patient following patient discharge, under an embodiment.

This, for example, may occur upon hospital discharge of a known patient who had been hospitalized for two weeks in acute congestive heart failure. FIG. 26 shows an example of the dMEMs from the perspective of the active practice physician when treating a patient following patient discharge, under an embodiment. The treating cardiologist, in this case, upon patient discharge may wish to continue to follow real-time heart indices post-discharge for two to three weeks. By extending real-time monitoring beyond the hospital stay to the treating physicians handheld or tablet device (perhaps even professional monitoring services), daily medication changes as may become needed would negate what would surely become a hospital re-admission for a similar non-monitored patient.

In another example, a 33-year old female patient is transferred from the Emergency Department to the Critical Care Unit after initial assessment indicates the patient has sustained multi-trauma from a motor vehicle accident one hour earlier. CT Scans on admit to the ER reveal no intra-abdominal or intra-cerebral bleeds, but renal, splenic and hepatic contusions are suspected. The patient has multiple rib fractures, and is breathing on her own and semi-comatose. The admitting Critical Care physician has been apprised of the patient's condition after reading the patient's electronic chart from the emergency department while the patient is in transit to the Critical Care Unit. Upon arrival he performs a complete physical exam. At that juncture, the physician notes the patient has already been identified and has been logged into Hospital's Cloud Port on the 3D Cloud platform.

Figure 27:
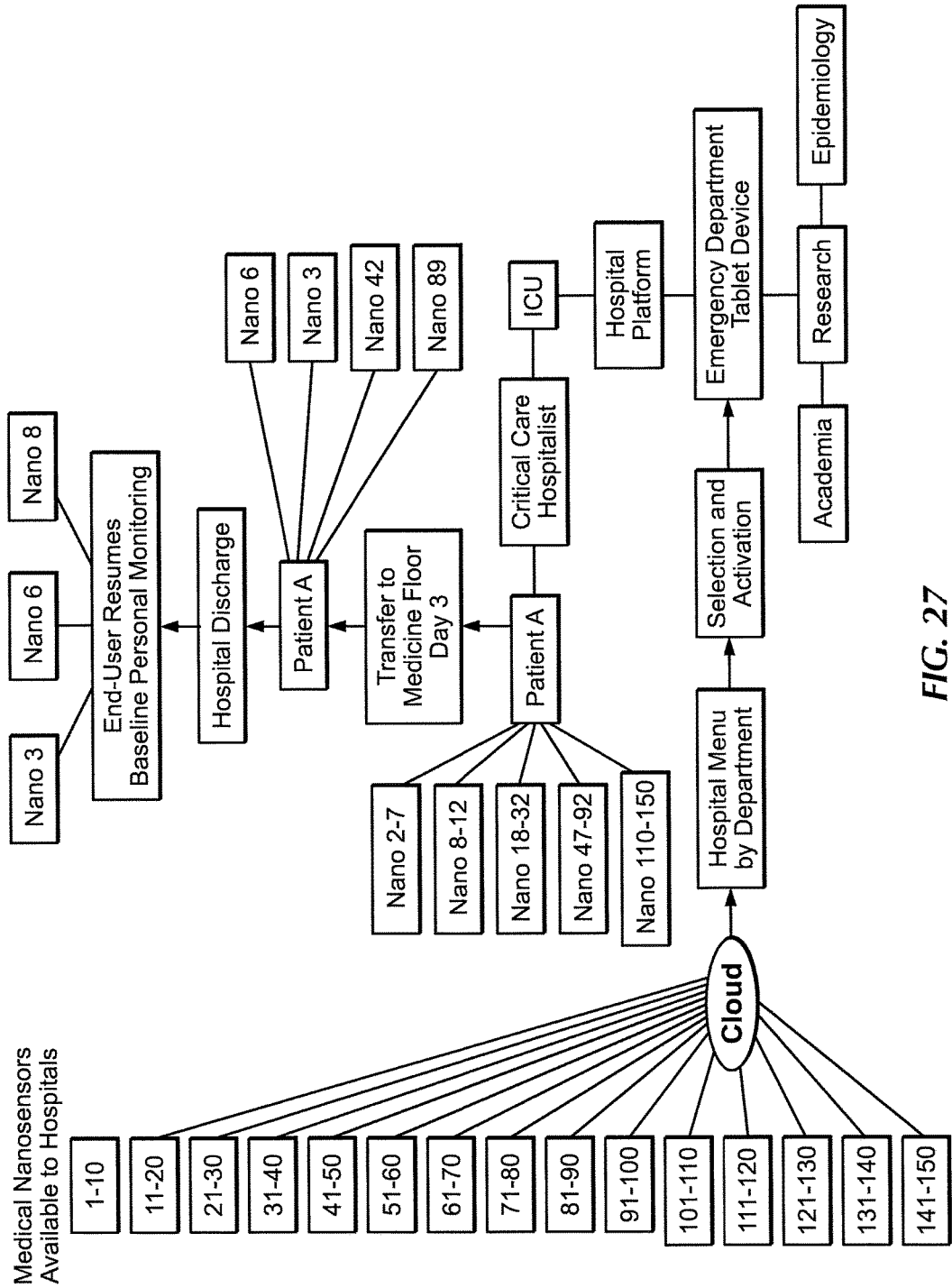
FIG. 27 shows an example of the dMEMs from the perspective of the active practice physician when treating critical care patient, under an embodiment.

From that point the physician determine what body systems are of most immediate importance to monitor. He will have a handheld tablet with a selection list of medical systems categorized app icons to choose from. The list will have hundreds of individual monitors to choose from as well as lists of single app consolidated nano-sensors. He will make his decision promptly and upon touchpad app selection he will be activating the helical cloud system for immediate recording and feedback. As each nano-sensor or consolidated group of nano-sensors is applied, immediate real-time bedside feedback monitoring is initiated from the Cloud. The physician may select upwards of 50 or more nano-sensors to monitor multi-body systems (e.g., real-time hepatic enzyme flows, cardiac enzymes, renal functions, etc.) all in an effort to preemptively monitor for latent contusional blood loss that could preemptively indicate pending catastrophic organ failure. As the patient's medical condition stabilizes and improves over the next 48 hours the numbers of acute admission (50) nano-sensor functions being monitored may be gradually pruned as condition allows. FIG. 27 shows an example of the dMEMs from the perspective of the active practice physician when treating critical care patient, under an embodiment. The above are just a few cited examples, and in no way are an indication of all potential systems users.

Figure 28:
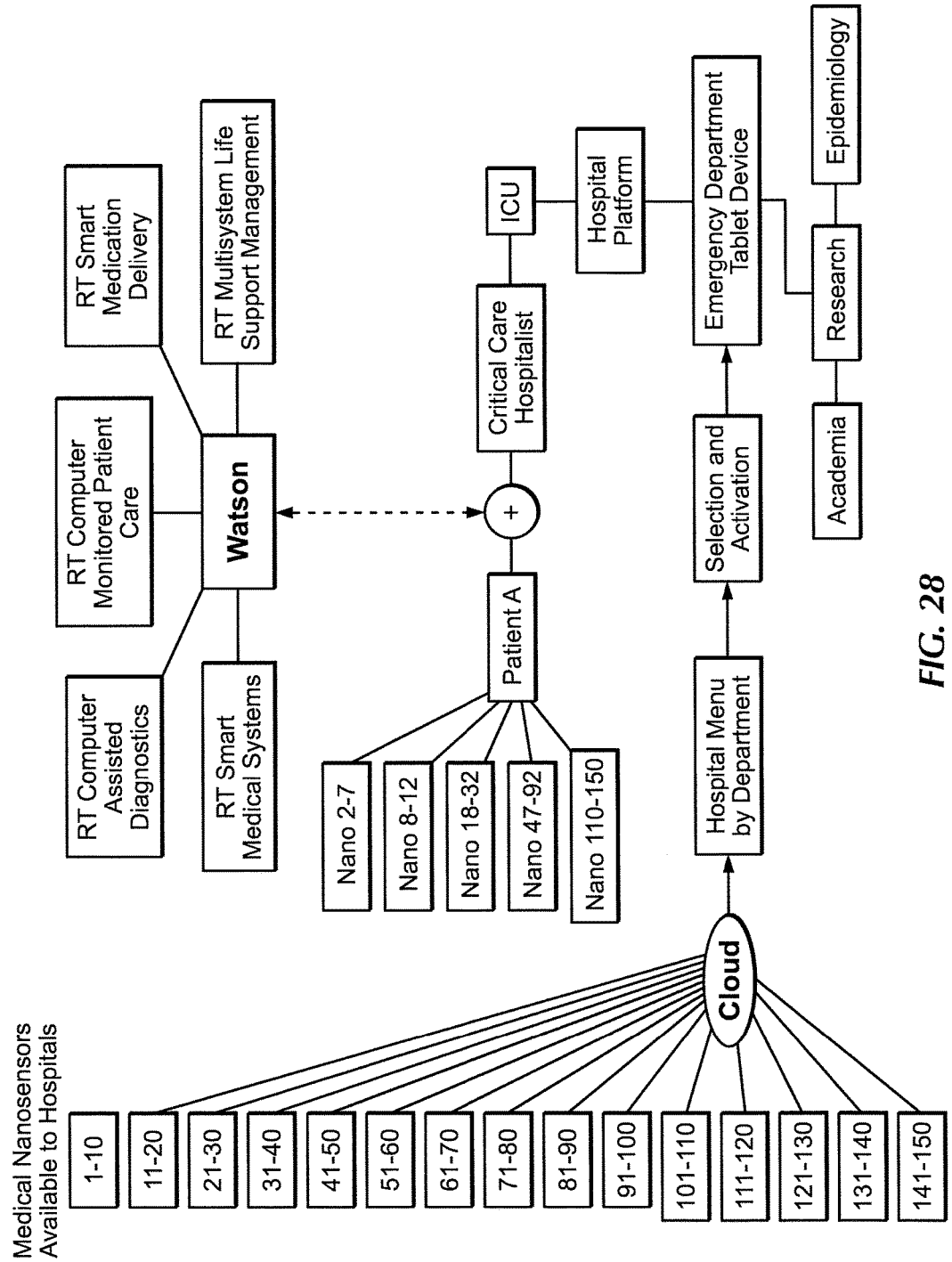
FIG. 28 is a block diagram of the dMEM integrated with medical smart systems, under an embodiment.

In the above case presentation the medically-necessary selections of nano-sensors were made by the attending acute care physician but embodiments are not so limited. It is promptly anticipated that near future joint venture projects with potential medical smart systems such as IBM's Watson, or comparable system, may allow for the integration of computer assisted diagnosing, as well as computer monitored patient care with eventual real-time computer to patient monitored management for multiple systems life support including medication delivery. FIG. 28 is a block diagram of the dMEM integrated with medical smart systems, under an embodiment.

Genesis of Early and Latent Intelligence

Probability modeling is considered key to the anticipated future arrival of Artificial General Intelligence. Previously, efforts to study causal generation of probability as it may apply to milestones in human evolutionary intelligence have not occurred. In the description that follows, probability models are used to constructively examine the distant-past pre-organic, pre-biologic, pre-conceptual, pre-conscious and pre-probabilistic beginning of human intelligence. In so doing, the cosmos' causal origins for the earth-bound effect of evolution may be found.

The modeling described herein comprises or at least relates to probability modeling that is integral to the arrival of Artificial General Intelligence. The following presents a description of artificial intelligence (AI) probability models to examine the roots of early intelligence as well as the connections and pathways to future AI.

Understanding the observer frame of reference, as it applies to inertia frames and non-inertia frames is paramount to a final understanding of context and content of the following description. The definitions that immediately follow correspond to a non-inertia frame of reference (non-inertial frames of reference when deemed necessary are denoted herein by "*") and are explicitly related to the perspective of an observer on the surface of earth i.e. celestial body:

The term "concept" as used herein includes but is not limited to something formed in the conscious mind, for example a thought or notion;

The term "conceptual" as used herein includes but is not limited to of, relating to, or based on conscious mental concepts;

The term "pre-conceptual" as used herein includes but is not limited to of, relating to, a period or time prior to the existence of consciousness, conscious thought, conscious mental concepts or conceptualization;

The term "random probability" as used herein includes but is not limited to of, relating to, or based on a conscious concept derived from a single present or prior mental or physical event;

The term "non-random recurring probability" as used herein includes but is not limited to of, relating to, or based on a conscious concept derived from relational prior mental or physical events; and The term "effectual probability" as used herein includes but is not limited to of, relating to, or based on conscious mental concept derived from a prior mental or physical event that can physically direct and/or act upon an immediate present or future physical event.

The definitions that immediately follow correspond to an inertial frame of reference (inertial frames of reference when deemed necessary are denoted herein by "**") and are explicitly related to an observer located in the open space of the cosmos:

The term "pre-conceptual" as used herein includes but is not limited to of, relating to, the sole interactions of physical components generating a conceptual figment that necessarily precedes any prior existence of consciousness, conscious thought, conscious mental concepts or conceptualization. It is the pre-evolutional cosmos' physical creation of a precursor to intelligence; and The term(s) "random and non-random recurring probability" as used herein may pre-conceptually appear as physical entities only (entropic forces upon mass).

The modeling described herein is based on a hypothesis that evolution emerged on earth as an effect, and its causal origins are to be found in a pre-evolutional cosmos devoid of the presence or benefit of probability, necessity, purpose, organization, memory or conscious intelligence. The description herein examines evolution as the beginning point of an effect (non-inertial frame of reference) rather than the point of origin of a cause (inertial frame of reference). To fully appreciate causation and effect under this conjecture, the onset of biologic evolution must necessarily be assessed one-step further removed from its own effectual origin to encounter a two-pronged causal beginning. This is accomplished by generating a thought experiment looking back to the distant-past spanning large expanses in an entropic driven cosmos from the perspective of earth-bound observers.

The top-down search for causation, is as follows:

A. De-construct the process of biologic evolution for an earth-bound observer by going back billions of years to the onset of earth's rotational cycles in an early post-accretion solar system;

B. From this effectual* point on earth in a post-accretion solar system, probability modeling as a tool is then used once again, looking further back to an entropic pre-biologic, pre-conceptual and pre-probabilistic environment in the late recombinant period**. At this point, particulate mass coalescing by action of linear and angular forces gives rise to large-scale galaxy and star formations in the cosmos. It is here that linear and angular entropic force acting upon a celestial body gives conceptual rise to random and non-random probability; C. These individually may be looked upon as a fictitious pre-conceptual effect that encompasses all celestial* bodies that are transitioning to a stabilized rotation;

D. These when acting in concert upon a celestial body in stable rotation become causal** leading to the onset of a celestial* effect with the eventual rise and propagation of evolutionally induced intelligence. (i.e., as has occurred on planetary earth).

This top-down dissection into an early entropic driven universe reveals a pre-evolutional, pre-biologic environment starkly devoid of the presence or benefits of necessity, purpose, organization, memory or intelligence. When mindfully re-constructing from a bottom-up perspective, energy and mass in motion are the only substrates available to build toward an effectual* evolutional earth model. Entropic forces acting upon celestial bodies give rise to minimal after-traces of occult probability as the rise of early randomness and later non-randomness generated in the after-wake of energy acting upon mass appear to be new found examples of conceptual fictitious forces/effects*. These subtle fictitious after-effects created by force acting upon mass are the only available bridging tools to advance a pre-evolutional physical environment to an evolutionally conceptual/intellectual one, and as such, these pre-conceptual-effects represent the earliest rudimentary principles for what later develops into intelligence**.

The fictitious generation of random and nonrandom recurring probability creates the link between the early physical and later conceptual, effectual and eventually intellectual. In bridging a bottom-up pre-evolutional** period to a post-evolutional* period, the two-pronged cosmic causals** of entropic driven primary randomness, and secondary non-randomness, when combined, become the drivers for the fictitious rise of a single, new-order tertiary* probability model that is effectual* as it allows and promotes conscious intelligence over accountable time. It is the beginning point of the process of evolution, as it is known.

The objectives include: identifying the pre-evolutional, inorganic, non-biologic physical antecedents that caused** the effectual* emergence of human intelligence on earth; and identifying and defining the pre-evolutional inorganic causes** and the post-evolutional inorganic/organic causes* that will lead to an effectual* emergence of artificial general intelligence on earth.

Considering the objectives, general probability modeling is mindfully applied and is used exclusively to compare, examine and categorize the components of our distant-past earth in a top-down non-inertial frame and then in a bottom-up inertial frame approach.

Regarding the top-down non-inertial frame in pursuit of an early post-evolutional environment, two distinct interacting models are encountered and referred to herein as the "Earth proper" (as a celestial body), and the "Distant Cosmos". The Earth proper (as a celestial body) is a stable surface environment serving as a potential self-contained cauldron capable of hosting an ongoing and infinite array of perpetual random occurrences (energy consuming/yielding of chemical, mechanical, electrical, and magnetic interreactions in varying states and transitions i.e. gaseous, liquid and solid). Note that random probability emerged on earth in an after-wake of entropic linear forces in a pre-evolutional cosmos, and is perpetual, but ineffectual as to future change.

The Distant Cosmos is a space continuum and as an entropic energy/power source influences earth's non-random recurring gravitational rotation in space. Note that non-random recurring probability emerged on earth in the sustained after-wake of entropic angular rotation in a pre-evolutional cosmos, and is perpetual, but is ineffectual as to future change.

Regarding the bottom-up inertial frame, from a pre-evolutional, pre-biologic, pre-conceptual perspective, two distinct models may be encountered. When using probability modeling to examine the earth, as a celestial body in a now pre-evolutional cosmos, two distinct pre-conceptual occurrences are again immediately recognized as random probability and non-random recurring probability. These are the result of causal entropic forces acting upon a rotating (1) earth in a physical (2) cosmos. Remarkably, these two fictitious "pre-concepts" are solely created by the after-wake effect of mass and energy in motion. They are denoted as, $$(a)+(b),$$

where (a) represents entropic linear-forces acting upon a celestial body/mass; create fictitious pre-conceptual randomness (primary), and (b) represents entropic angular-forces acting upon a celestial body/mass; create fictitious pre-conceptual non-randomness (secondary).

Some 4.6 billion years ago the solar system was in the process of forming by accretion. It is likely that during this period the pre-evolutional interaction of celestial bodies i.e. the (1) earth and forces of the (2) cosmos, gave rise in an "after-wake" effect of linear and angular entropic forces to the individual generation of causal (a) randomness, and (b) non-randomness on (1) earth. FIG. 29A shows entropic linear-forces acting upon a celestial body/mass; create fictitious pre-conceptual randomness (primary). FIG. 29B shows entropic angular-forces acting upon a celestial body/mass; create fictitious pre-conceptual** non-randomness (secondary).

FIG. 30 is a depiction of the pre-evolutional graphic of the (1) earth moving within the forming universe's accretion disk as a chaotic celestial body transitioning to [(a)+(b)], where (a) represents a cosmic linear entropic force and (b) represents a cosmic angular entropic force, as described herein. FIG. 31 demonstrates the transition in the late accretion period to (c) (tertiary). The sustained "after-wake" effect of cosmic entropic force acting upon [(a)+(b)] results in the energy-driven transition to (c); only when the celestial** body i.e. earth in this case, experiences aligned linear and angular forces that are perpendicular. FIG. 32 depicts the sustained "after-wake" effect of cosmic entropic force acting upon [(a)+(b)] and producing the energy-driven transition to (c). The tertiary state is ultimately the end-result and represents the earth's* point of entry into a stable energy driven post-evolutional era giving rise to the creation of a higher-order tertiary* probability with a fictitious force/effect that is now consistent with and capable of generating effectual* probability.

Figure 33:
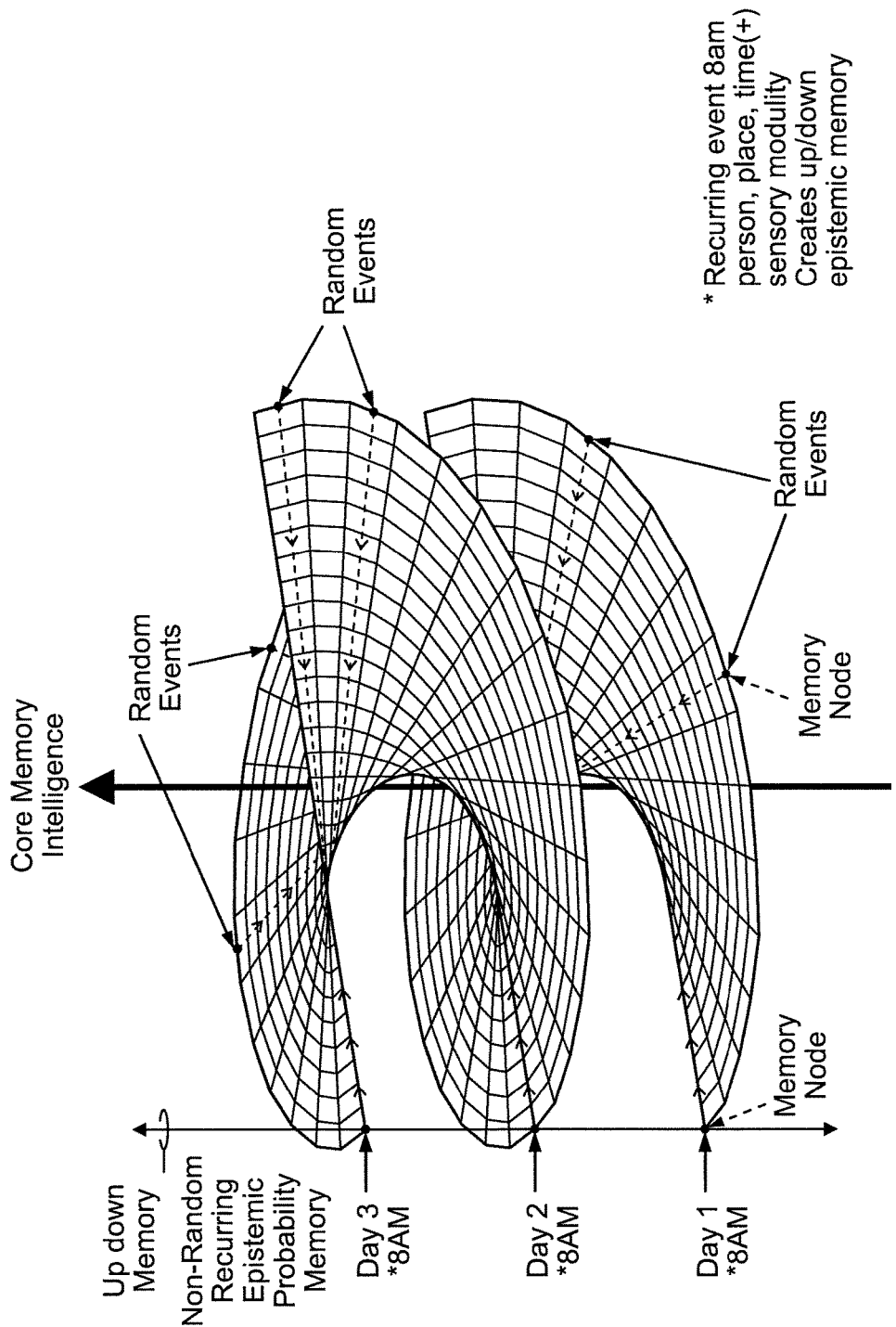
FIG. 33 depicts a helicoid matrix of core memory intelligence development.

With the perpetual constancy of causal entropic forces acting upon earth* (i.e. linear and angular forces) the resulting after-wake of perpendicularly aligned [(a)+(b)] necessarily transition to a standing energy driven vortical helix denoted as (c). The use of a helical analogy allows and defines the pre-evolutional/post-evolutional point where the fictitious effects of entropy driven pre-conceptual random and pre-conceptual non-random merge as they move to a single tertiary-order* probability model (R-N-R and N-R-N). The tertiary probability* model that is created conceptually, perceptually and effectually establishes accountable time (t) on earth. The then recurring 24-hour circadian sequencing of 1(c) immediately transitions to 1(c)/t as it becomes a directional thermodynamic time arrow. It is the unification of pre-conceptual random and nonrandom probability in the after-wake of causal entropic forces acting upon celestial mass that creates this perpetual helicoidal matrix that enables development over billions of years of organic intelligence*, as up/down memory and purposeful predictive intelligence now become conceptually, perceptually and effectually possible across time. FIG. 33 depicts a helicoid matrix of core memory intelligence development.

The slow but progressive multi-billion year rise of conscious* biologic intelligence in response to the (c)t perpetual chaos and uncertainty necessarily occurs due to the nature of incremental genetically accrued intelligence. Having now arrived to this point, the human creation and propagation of AGI will not be subject to such.

It is the causal interaction of the pre-evolutional tangibles** of cosmic entropic linear, angular and rotational forces acting in concert with cosmic mass in motion, that create an accountable real-time tertiary-probability on earth. Tertiary-Probability* as a pre-evolutional/post-evolutional "effect" establishes the earth's biologic beginning point for the conceptual and perceptual rise of the cognitively effectual intangibles of accountable time, probability, organization, memory, purpose and progressive intelligence. Any major change or disruption relative to the tangibles** of the (1) earth or the (2) cosmic entropic forces acting upon it; and the after-wake-energy-driven-effects of the intangibles* of (c)/t will immediately vanish.

It is the action and interactions of causal entropic force(s) upon mass within a non-biologic pre-evolutional cosmos** that gives rise to tertiary effectual* probability (aka evolution) on earth. It is this what bridges the tangibles of the cosmos to the cognitive intangibles of (early) Human and (latent) Artificial Intelligence on earth (i.e. as cognitive science and computational science).

Simple probability is encountered and dealt with in our present everyday lives. It has for many centuries been a wholly incomplete under-recognized science due to the nature of it's conflicting premises; both of which are correct, but paradoxically oppositional as to the perspectives of the frequentist versus epistemic. In reality, both are the pre-conceptual/conceptual** precursors to entropy driven tertiary effectual* probability. Probability studies, when looked upon as primary random (frequentists) and secondary non-random probability (epistemic) are first and second order conceptual entities and as such are confined to past and present events. It is tertiary effectual probability that gives rise to accountable time and has direct and indirect effects and influence over future events.

Utilizing the conceptual analogy of the helicoidal model (FIG. 33), the precursors of primary and secondary conceptual probability, as well as tertiary effectual probability are graphically plotted.

Even when considering the mindful introduction as given herein, the actual catalysts that initiated earthly intelligence in our everyday lives remains all but hidden. Much like Aristotle's "unmoved mover", one must fully examine and observe the process of ongoing evolution in motion and over time by combining the clockwork interactions of (1) earth and (2) cosmos as above. To the cognizant observer on earth, the dynamic conceptual components and effectual consequences of the physical interaction of the earth within the solar system are no more obvious to that end-observer, as the meaningless motions of the second hand of a desk clock are to the eyes of the immature three-year old child.

To perhaps now appreciate the perspective of this unique earth phenomena, one need only to remove and or significantly alter a single physical component, gear, or cog in the perpetual "clockwork" process defined by (1) earth and (2) cosmos as described above (i.e. entropic driven mass in motion), and the process will necessarily come to a disintegrating halt (going from a single tertiary helicoidal "effectual model" back to separate disparate systems of (a) random linear and (b) non-random circular/angular probability devoid of effect or time).

By way of mindful probability modeling a similar phenomena with both "conceptual and effectual consequences" is reproducible on a micro-earth scale when a mechanical wind-up desk clock is studied from across a room as it sits on a desktop. The running clock, as a kinetic (entropy) driven microcosm, mechanically represents (1) earth and (2) cosmos as it occupies space as mass and is moving in response to the concerted forces of energy. In so doing, it parallels the cosmic entropic changes of [(a)+(b)] transitioning to (c)t. From the perspective of the cognizant observer, the isolated desk clock has "effectual consequences" (tertiary effectual probability) and may influence future events, creating necessity and purpose for cognitive actions. Should the force of it's kinetic energy suddenly dissipate (i.e. spring physically breaks or it simply runs down), the system immediately implodes to (1) and (2) with the spontaneous disappearance of the energy driven dynamics of [(a)+(b)] and the immediate loss of the fictitious forces/effects of (c)t. From that moment on, the clock no longer has conceptual purpose for the cognitive in room observer relative to the past, and no longer imposes effectual probability for present or future cognitive actions. The dormant clock does no more than inertly occupy space.

Furthermore, if two identical mechanical desk clocks are placed running side by side on the same desk, both clocks yield consecutive moment by moment information with their respective "1c/t" functionalities in-place and intact. Both clocks would then be capable of providing "conceptual insight & effectual consequences" for the cognizant soul, as they impart an understanding of the past, and give purpose to present and future, place, time and events. Now suppose in this scenario that after two hours one of these clocks without prior notice winds-down or breaks and the other continues to run.

In the previous two hours, when running side by side both clocks yielded consecutive, concurrent, moment by moment information with their respective "c" functionality in-place and intact. Both provided tertiary order effectual probability giving purpose to present and future time, place(s) and events for the cognizant in room observer. With one of the two clocks stopping, the pre- and post-residual "conceptual insight and effectual consequences" have dramatically changed. The stopped clock not only sustained a complete and immediate loss of it's concerted physical function, but also the complete and immediate loss of it's in-place capacity as a generator of "c". At that instant, it no longer conveyed or harnessed the prowess of [(a)+(b)] and offers no real conceptual hindsight nor purpose, and imposes no effectual or insightful consequence on the present or future environment other than occupying space.

Had the two clocks been acting in parallel, they could well have been monitoring two different, conceptually purposeful places, times and events with effectual future consequences/outcomes of each controlled by the cognizant in-room observer. For example, an observing and inquisitive three year old child looking on from his grandfather's knee, the sudden stoppage of the clock would likely create only a momentary look of astonishment (as the young child recognizes only essential random probability of the event i.e. clock stops), a conceptual none-event only as the child has not developed an appreciation for non-random recurring epistemic probability. However, the experienced train yard manager on his evening shift (at the moment the clock stopped) would likely jump up from his train yard perch to immediately sound the alarm shutting down the railroad yard in order to avert catastrophe. The grandfather in this instance recognizes the past and present conceptual probability of the event i.e. potential catastrophe (a result of past epistemic conceptual non-random recurring probability). His then present and immediate sounding of the alarm is a cognitive physical event directed by tertiary effectual probability to avert another physical event at a future place and time.

This is initiated and accomplished by "effectual probability" (epistemic probability now looking to the future) as it demonstrates how an intangible cognitive process may be used to bridge and act upon two different physical events, one present and one future. Tertiary effectual probability is essentially the intangible of cognitive intelligence physically acting upon a future environment/or event to reduce present and future physical chaos and uncertainty (in a wholly motion filled physical world). So in other words, a loss of two to five minutes on consecutive rail yard track clocks, each set to follow one of two moving trains coming into the yard from different directions, could prove calamitous.

It is only when this inert broken-clock model of evolution is fully dissected and considered alongside and parallel to the functional model, that the seemingly subtle traces of disparate probabilities that create "(c)t," may be recognized, appreciated, and then conceptually and effectually understood from the bottom-up. The fictitious effects of conceptual and effectual probability first appeared on our distant-past timeline at the inception and establishment of earth's seemingly stable circular circadian rotation in the early solar system's post-accretion period:

When: $(1)^* + 2(a) + (b)^{**}$, goes to $1(a) + (b)^* + 2^{**}$, goes to $1(c)t^* + 2^{**}$.

The model above represents an evolving functional earth* and it's relative position in the solar system** as, $1(a)^* + 1(b)^* = 1(c)t^*$, represents a functional earth*. It is likely that forces acting upon our * frame of reference, such as the Coriolis effect, the centrifugal, rectilinear or Euler force, or perhaps Frenet-Serret frames or rotation in a frame tied to the Universe may act as the repository for the fictitious conceptual effects/forces of effectual tertiary probability(s) that surround us as:

$1(c)/t$

By applying Occam's Razor in simplest form, intelligence* is the result of causal** entropic forces acting upon mass yielding tertiary probability* in anticipation of future chaos and uncertainty. By applying Occam's Razor, it is put forth that the source of our ancestral intelligence on earth* came about as the result of causal** omnipresent entropic forces acting upon celestial bodies within a pre-evolutional cosmos devoid of organization, probability, necessity, purpose, memory and intelligence. The resultant fictitious forces/effects of tertiary probability* acting upon earth* gave rise to purpose, complex memory, the effectual perception of accountable time, human intelligence (early) and artificial intelligence (latent); all in order to preemptively anticipate and lessen future chaos and uncertainty.

The analysis herein concludes that $1(a) + (b)$, goes to $1(c)/t$, where causal entropic forces in a pre-evolutional cosmos** devoid of concept, probability, necessity, purpose, organization, memory or intelligence gave rise to celestial* (a) random and (b) non-random probability. The process of evolution on earth came to be with the entropic emergence of effectual tertiary probability $1(c)/t$, therefore evolution managed to create intelligence without the use of intelligence.

For humanity to model and or copy one of nature's truly vexing and complex processes, the etiological origins must first be fully vetted, sorted and understood, inclusive of the pre-founding antecedent principles which bring it about. As genetically bound entities, the present accrued intelligence has clearly seen a long and arduous journey whose successive chains of organic evolution and eventual rise to its' present level of complexity necessarily had to occur over a multi centi-million year span.

Evolution's unrelenting primary effectual push for genetically accrued Human Intelligence has not only now given-up and defined the pre-evolutional past point of origin, but it also provides the accrued knowledge and the retrospective proof of concept "source code" to now go forward into a latent secondary effectual era, with the genesis of Artificial Intelligence. By understanding the antecedent point of origin 1(c)/t, the progressive evolution over millions of years has physically arrived to have sufficient collective intelligence to perceptually and conceptually create evolution's ultimate effectual goal: artificial intelligence.

Evolution, as a dynamic organic process, has allowed perpetual earth-bound "random probability/events" to occur at all levels, although it is most apparent at particle, atomic, and molecular levels. A gradual hierarchal transition into "non-random recurring probability/events" is most evident at higher functional levels as occurs in organized cells, higher organic life, and social organization. Both are perpetual and both must be present before an organic-hierarchy for functional intelligence via tertiary effectual probability may be attained.

The pre-evolutional** of 1(a)+1(b) going to 1(c)t* in the model described herein, allows for the coexistence of determinate and non-determinate components, thereby perhaps appeasing, both classic and quantum physics. As a helicoidal (helical) continuum, 1(c)t may be sequentially compressed to an elegantly simple and singular algorithm.

Embodiments described herein include a method comprising receiving in real-time data of a plurality of parameters representing an entity. The method comprises generating micro plots that each comprise a plot of the data for a corresponding time period of a plurality of time periods. Each time period is cyclical. The method comprises generating a model plot comprising the micro plots plotted chronologically according to the plurality of time periods. The model plot comprises a continuous helix. The method comprises generating a prediction of a state of the entity using characteristics of the model plot.

Embodiments described herein include a method comprising: receiving in real-time data of a plurality of parameters representing an entity; generating micro plots that each comprise a plot of the data for a corresponding time period of a plurality of time periods, wherein each time period is cyclical; generating a model plot comprising the micro plots plotted chronologically according to the plurality of time periods, wherein the model plot comprises a continuous helix; and generating a prediction of a state of the entity using characteristics of the model plot Embodiments described herein include a method comprising receiving physiological data that includes data of a plurality of physiological parameters collected from an individual entity. The method comprises generating a plurality of micro plots. Each micro plot comprises a cyclical plot of the physiological data for a corresponding time period. Each micro plot corresponds to a time period of a plurality of time periods. The method comprises generating a medical model plot comprising the plurality of micro plots. The plurality of micro plots is plotted chronologically according to the plurality of time periods. A location of an endpoint of each micro plot determines a change in slope of the medical model plot. The slope represents a state of health of the individual entity.

Embodiments described herein include a method comprising: receiving physiological data that includes data of a plurality of physiological parameters collected from an individual entity; generating a plurality of micro plots, wherein each micro plot comprises a cyclical plot of the physiological data for a corresponding time period, wherein each micro plot corresponds to a time period of a plurality of time periods; and generating a medical model plot comprising the plurality of micro plots, wherein the plurality of micro plots are plotted chronologically according to the plurality of time periods, wherein a location of an endpoint of each micro plot determines a change in slope of the medical model plot, wherein the slope represents a state of health of the individual entity.

The physiological data is collected in real-time from sensors coupled to the individual entity.

The sensors comprise nano-sensors.

The sensors comprise sensors coupled to the individual entity.

The sensors comprise sensors implanted in the individual entity.

The method comprises continuously collecting the physiological data.

The physiological data comprises time data.

The physiological data comprises location data.

The physiological data comprises physical activity data.

The time period of the cyclical plot is a 24-hour period.

The cyclical plot is based on a circadian cycle.

The micro plot for each time period comprises a start point and the endpoint.

The endpoint of each micro plot is located at a same point in a complete rotation that defines the micro plot.

The endpoint of each micro plot for each time period is located at a new position in space.

The physiological data determines the new position of the endpoint.

The endpoint of a micro plot is a start point for a next subsequent micro plot.

The medical model plot comprises a continuous helix comprising the plurality of micro plots.

The method comprises compressing the data of the plurality of micro plots to form the medical model plot.

The method comprises determining the state of health by comparing at least one set of micro plots of the medical model plot.

Changes in the slope indicate physical changes in the state of health of the individual entity.

The slope of the medical model plot is inversely proportional to a quality of life of the individual entity.

The slope of the medical model plot represents longevity of the individual entity.

The medical model plot comprises a start point that corresponds to birth of the individual entity.

The medical model plot comprises a normal zone, wherein the normal zone represents absence of disease process in the individual entity.

The medical model plot comprises a subclinical zone, wherein the subclinical zone represents onset of clinical symptoms in the individual entity.

The medical model plot comprises a clinical zone, wherein the clinical zone represents presence of clinical symptoms in the individual entity.

The medical model plot comprises an endpoint that corresponds to death of the individual entity.

The method comprises providing the medical model plot to the individual entity.

The method comprises providing the medical model plot to at least one healthcare provider.

The method comprises providing the medical model plot to at least one organization.

Embodiments described herein include a system comprising a plurality of sensors coupled to an individual entity. The plurality of sensors collects physiological data that includes data of a plurality of physiological parameters collected from the individual entity. The system includes a platform comprising a processor. The platform is coupled to the plurality of sensors. The processor is running an application, and the application generates a plurality of micro plots. Each micro plot comprises a cyclical plot of the physiological data for a corresponding time period. Each micro plot corresponds to a time period of a plurality of time periods. The application generates a medical model plot comprising the plurality of micro plots. The plurality of micro plots is plotted chronologically according to the plurality of time periods. A location of an endpoint of each micro plot determines a change in slope of the medical model plot. The slope represents a state of health of the individual entity.

Embodiments described herein include a system comprising: a plurality of sensors coupled to an individual entity, wherein the plurality of sensors collect physiological data that includes data of a plurality of physiological parameters collected from the individual entity; and a platform comprising a processor, wherein the platform is coupled to the plurality of sensors, wherein the processor is running an application, wherein the application generates a plurality of micro plots, wherein each micro plot comprises a cyclical plot of the physiological data for a corresponding time period, wherein each micro plot corresponds to a time period of a plurality of time periods, wherein the application generates a medical model plot comprising the plurality of micro plots, wherein the plurality of micro plots are plotted chronologically according to the plurality of time periods, wherein a location of an endpoint of each micro plot determines a change in slope of the medical model plot, wherein the slope represents a state of health of the individual entity.

The physiological data is collected in real-time from the plurality of sensors.

The sensors comprise nano-sensors.

The sensors comprise sensors coupled to the individual entity.

The sensors comprise sensors implanted in the individual entity.

The system comprises continuously collecting the physiological data.

The physiological data comprises time data.

The physiological data comprises location data.

The physiological data comprises physical activity data.

The time period of the cyclical plot is a 24-hour period.

The cyclical plot is based on a circadian cycle.

The micro plot for each time period comprises a start point and the endpoint.

The endpoint of each micro plot is located at a same point in a complete rotation that defines the micro plot.

The endpoint of each micro plot for each time period is located at a new position in space.

The physiological data determines the new position of the endpoint.

The endpoint of a micro plot is a start point for a next subsequent micro plot.

The medical model plot comprises a continuous helix comprising the plurality of micro plots.

The data of the plurality of micro plots is compressed, and the medical model plot comprises the compressed data.

The state of health by is determined by comparing at least one set of micro plots of the medical model plot.

The change in the slope corresponds to physical changes in the state of health of the individual entity.

The slope of the medical model plot is inversely proportional to a quality of life of the individual entity.

The slope of the medical model plot corresponds to longevity of the individual entity.

The medical model plot comprises a start point that corresponds to birth of the individual entity.

The medical model plot comprises a normal zone, wherein the normal zone represents absence of disease process in the individual entity.

The medical model plot comprises a subclinical zone, wherein the subclinical zone represents onset of clinical symptoms in the individual entity.

The medical model plot comprises a clinical zone, wherein the clinical zone represents presence of clinical symptoms in the individual entity.

The medical model plot comprises an endpoint that corresponds to death of the individual entity.

The medical model plot is provided to the individual entity.

The medical model plot is provided to at least one healthcare provider.

The medical model plot is provided to at least one organization.

Computer systems and networks suitable for use with the dMEM embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network as a component of progressive mechanical intelligence embodiments may be any microprocessor controlled device that permits access to the network, including terminal devices, such as personal computers, workstations, servers, mini computers, main-frame computers, laptop computers, mobile computers, palm top computers, hand held computers, mobile phones, TV set-top boxes, or combinations thereof. The computer network may include one of more LANs, WANs, Internets, and computers. The computers may serve as servers, clients, or a combination thereof.

The dMEM can be a component of a single system, multiple systems, and/or geographically separate systems. The dMEM can also be a subcomponent or subsystem of a single system, multiple systems, and/or geographically separate systems. The dMEM can be coupled to one or more other components (not shown) of a host system or a system coupled to the host system.

One or more components of the dMEM and/or a corresponding system or application to which the dMEM is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that includes the dMEM can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or back-end networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the dMEM and corresponding systems and methods is not intended to be exhaustive or to limit the systems and methods to the precise forms disclosed. While specific embodiments of, and examples for, the dMEM and corresponding systems and methods are described herein for illustrative purposes, various equivalent modifications are possible within the scope of the systems and methods, as those skilled in the relevant art will recognize. The teachings of the dMEM and corresponding systems and methods provided herein can be applied to other systems and methods, not only for the systems and methods described above. The elements and acts of the various embodiments described above can be combined to provide further embodiments. These and other changes can be made to the dMEM and corresponding systems and methods in light of the above detailed description.

What is claimed is:

1. A method comprising:
    configuring a plurality of nanosensors to be carried at least one of on and in an entity and to collect data of a plurality of parameters representing the entity;
    receiving in real-time the collected data of the plurality of parameters via a telemetry link from the plurality of nanosensors;
    generating micro plots that each comprise a plot of the collected data for a corresponding time period of a plurality of time periods, wherein each micro plot integrates the collected data for the time period into a cyclical plot of the plurality of parameters, wherein a location of an endpoint of each micro plot is determined by individual values of the plurality of parameters of the collected data;
    generating a model plot comprising a life cycle line, wherein the life cycle line includes a continuous helix formed by consecutively plotting the micro plots in chronological order according to the plurality of time periods, wherein a slope of the life cycle line is determined by the locations of the endpoints of the micro plots and correlates to actions and behaviors of the entity during the plurality of time periods; and
    predicting with the slope of the life cycle line medical profiles of the entity for future time periods beyond the plurality of time periods, wherein a decrease in the slope indicates at least one of better quality of life and longer life, and an increase in the slope indicates at least one of worse quality of life and shorter life, wherein the medical profiles include predictions of physiological event data at future time periods in the life of the entity, and outputting the prediction for use in preventative treatment of the entity.

2. The method of claim 1, comprising continuously collecting the data of the plurality of parameters.

3. The method of claim 1, wherein the data of the plurality of parameters comprises time data, location data, physiological data, and physical activity data.

4. The method of claim 1, wherein the time period is a 24-hour period.

5. The method of claim 1, wherein the cyclical plot is based on a circadian cycle.

6. The method of claim 1, wherein the endpoint of each micro plot for each time period is located at a position in space as determined by data of the plurality of parameters of that time period.

7. The method of claim 6, wherein the endpoint of a micro plot is a start point for a next subsequent micro plot.

8. The method of claim 7, comprising compressing the data of the plurality of micro plots to form the medical model plot.

9. The method of claim 1, comprising determining a state of health of the entity by comparing at least one set of micro plots of the medical model plot.

10. The method of claim 1, wherein changes in the slope indicate physical changes in the state of health of the individual entity.

11. The method of claim 1, wherein the slope of the model plot is inversely proportional to a quality of life of the individual entity.

12. The method of claim 1, wherein the slope of the model plot is configured to represent longevity of the individual entity.

13. The method of claim 1, wherein the model plot comprises a start point configured to correspond to birth of the individual entity.

14. The method of claim 13, wherein the model plot comprises a normal zone configured to represent absence of disease process in the individual entity.

15. The method of claim 14, wherein the model plot comprises a subclinical zone configured to represent onset of clinical symptoms in the individual entity.

16. The method of claim 15, wherein the model plot comprises a clinical zone configured to represent presence of clinical symptoms in the individual entity.

17. The method of claim 1, wherein the model plot comprises an endpoint configured to correspond to death of the individual entity.

18. The method of claim 1, comprising outputting the medical model plot to at least one of the entity and at least one healthcare provider.

* * * * *